United States Patent
O'Brien et al.

(10) Patent No.: US 11,426,180 B2
(45) Date of Patent: Aug. 30, 2022

(54) TISSUE PENETRATING SURGICAL SYSTEMS AND METHODS

(71) Applicant: University College Cork—National University of Ireland Cork, Cork (IE)

(72) Inventors: Peter Andrew O'Brien, Belgooly (IE); Matthieu Francois Gabriel Duperron, Savigny-sur-Orge (FR); Ray Burke, Whitechurch (IE); Cormac James Eason, Casteltroy (IE); Kevin Manley, Cobh (IE); Gerard Nunan, Ballincolig (IE)

(73) Assignee: University College Cork—National University of Ireland Cork, Cork (IE)

( * ) Notice: Subject to any disclaimer, the term of this patent is extended or adjusted under 35 U.S.C. 154(b) by 91 days.

(21) Appl. No.: 16/636,561

(22) PCT Filed: Aug. 3, 2018

(86) PCT No.: PCT/IB2018/055874
§ 371 (c)(1),
(2) Date: Feb. 4, 2020

(87) PCT Pub. No.: WO2019/026049
PCT Pub. Date: Feb. 7, 2019

(65) Prior Publication Data
US 2021/0153876 A1    May 27, 2021

Related U.S. Application Data

(60) Provisional application No. 62/541,339, filed on Aug. 4, 2017.

(51) Int. Cl.
*A61B 17/16* (2006.01)
*A61B 90/00* (2016.01)
*A61B 17/00* (2006.01)

(52) U.S. Cl.
CPC ........ *A61B 17/1626* (2013.01); *A61B 17/162* (2013.01); *A61B 17/1615* (2013.01);
(Continued)

(58) Field of Classification Search
CPC . A61B 17/16; A61B 17/1615; A61B 17/1617; A61B 17/162; A61B 17/1622;
(Continued)

(56) References Cited

U.S. PATENT DOCUMENTS 5,460,182 A * 10/1995 Goodman ............ A61B 5/0084
600/342
5,769,791 A * 6/1998 Benaron ............... A61B 5/0084
600/473

(Continued)

FOREIGN PATENT DOCUMENTS

DE    102011111671 A1    2/2013
EP       1741394 A1    1/2007
(Continued)

OTHER PUBLICATIONS

Augustin, Goran et al., "Cortical Bone Drilling and Thermal Osteonecrosis", Clinical Biomechanics, vol. 27, 2012, pp. 313-325.
(Continued)

*Primary Examiner* — Eric S Gibson
(74) *Attorney, Agent, or Firm* — Howard & Howard Attorneys PLLC

(57) ABSTRACT

A surgical system for penetrating and determining a characteristic of tissue. An instrument generates rotational torque, and a drill bit tool body extends along an axis between a distal end to engage tissue and a proximal end to couple to the instrument. An emitter operatively coupled to the instrument emits light. A detector operatively coupled to the instrument detects light. An emission lightguide within the tool body transmits light emitted by the emitter toward (Continued)

the tissue as the instrument rotates the tool body. A detection lightguide within the tool body is spaced from the emission lightguide and transmit light reflected by the tissue toward the detector as the instrument rotates the tool body. The emitter emits light into the emission lightguide along the axis, and the detector detects light reflected from the tissue exiting the detection lightguide transverse to the axis when the tool body is coupled to the instrument.

21 Claims, 24 Drawing Sheets

(52) U.S. Cl.
CPC ............... *A61B 2017/00057* (2013.01); *A61B 2090/062* (2016.02); *A61B 2090/08021* (2016.02)

(58) Field of Classification Search
CPC ............ A61B 17/1624; A61B 17/1626; A61B 17/1628; A61B 17/1631; A61B 17/1633; A61B 2017/00057; A61B 2017/00061
See application file for complete search history.

(56) References Cited

U.S. PATENT DOCUMENTS

| | | | |
|---|---|---|---|
| 5,772,597 A | 6/1998 | Goldberger et al. | |
| 5,843,000 A | 12/1998 | Nishioka et al. | |
| 5,987,346 A * | 11/1999 | Benaron | A61B 5/0059 600/407 |
| 6,085,121 A | 7/2000 | Stern | |
| 6,419,484 B1 * | 7/2002 | DaSilva | A61B 5/0066 433/29 |
| 7,901,400 B2 | 3/2011 | Wham et al. | |
| 8,038,693 B2 | 10/2011 | Allen | |
| 8,249,696 B2 | 8/2012 | Fisher et al. | |
| 8,463,421 B2 | 6/2013 | Brett et al. | |
| 8,535,340 B2 | 9/2013 | Allen | |
| 8,535,341 B2 | 9/2013 | Allen | |
| 8,894,654 B2 * | 11/2014 | Anderson | A61B 17/17 606/80 |
| 8,986,292 B2 * | 3/2015 | Sliwa | A61B 5/0075 606/15 |
| 9,113,900 B2 | 8/2015 | Buysse et al. | |
| 9,114,226 B1 | 8/2015 | Lash et al. | |
| 9,193,022 B1 * | 11/2015 | Janicki | B23B 49/00 |
| 2005/0116673 A1 * | 6/2005 | Carl | A61B 17/1626 318/432 |
| 2009/0221922 A1 * | 9/2009 | Lec | A61B 5/0084 600/478 |
| 2009/0299439 A1 | 12/2009 | Mire et al. | |
| 2009/0326537 A1 * | 12/2009 | Anderson | A61B 17/17 606/80 |
| 2011/0196376 A1 | 8/2011 | Ozgur | |
| 2012/0120256 A1 | 5/2012 | Hwang et al. | |
| 2012/0150170 A1 | 6/2012 | Buysse et al. | |
| 2012/0232407 A1 | 9/2012 | Fisher et al. | |
| 2012/0265184 A1 * | 10/2012 | Sliwa | A61B 5/0084 606/15 |
| 2012/0271176 A1 * | 10/2012 | Moghaddam | A61B 5/4542 600/476 |
| 2020/0367913 A1 * | 11/2020 | Forstein | A61B 17/1626 |
| 2021/0153876 A1 * | 5/2021 | O'Brien | A61B 17/162 |

FOREIGN PATENT DOCUMENTS

| | | |
|---|---|---|
| JP | 2012228510 A | 11/2012 |
| JP | 2015125046 A | 7/2015 |
| WO | 9741777 A1 | 11/1997 |
| WO | 9827865 A1 | 7/1998 |
| WO | 2007006698 A1 | 1/2007 |
| WO | 2009085492 A2 | 7/2009 |
| WO | 2009111387 A1 | 9/2009 |
| WO | 2010039316 A1 | 4/2010 |
| WO | 2012009040 A1 | 1/2012 |
| WO | 2012153084 A2 | 11/2012 |
| WO | 2014159889 A1 | 10/2014 |

OTHER PUBLICATIONS

Abstract of Bertollo, Nick et al., "A Comparison of the Thermal Properties of 2- and 3- Fluted Drills and the Effects on Bone Cell Viability and Screw Pull-Out Strength in an Ovine Model", Clinical Biomechanics, vol. 25, Issue 6, pp. 613-617, Jul. 2010, 1 page.

Duperron, Matthieu et al., "Diffuse Reflectance Spectroscopy Implemented Into a Drill for Bone Boundary Ahead Detection", Optical Society of America, 2017,11 pages.

English language abstract and machine-assisted English language translation for JP 2012-228510 extracted from espacenet.com database on Mar. 11, 2020, 19 pages.

Hassan, Muhamad Khairul Ali et al., "A Study of Bone Thickness Measurement by Using Infrared Sensor for Pedicle Screw Insertion", IEEE International Conference on Systems, Man and Cybernetics, 2013, pp. 2152-2156.

International Search Report for Application No. PCT/IB2018/055874 dated Apr. 9, 2019, 3 pages.

Li, Weitao et al., "Measurement System of Optical Properties of Vertebra Bones on Near-Infrared Spectrum", IEEE Conference on Orange Technologies, 2013, pp. 111-114.

Machine-Assisted English language abstract and machine-assisted English language translation for DE 10 2011 111 671 extracted from espacenet.com database on Mar. 11, 2020, 16 pages.

Rai, D. et al., "Spectrophotometric Analysis of Cortical Bone", IEEE Engineering in Medicine and Biology, 1991, p. 50.

Stringer, M. et al., "A TH-z Time Domain Study of Human Cortical Bone", 12th Annual International Conference on Terahertz Electronics, 2004, pp. 735-736.

Taroni, P. et al., "Time-Resolved Diffuse Optical Spectroscopy of Small Tissue Samples", Optics Express, vol. 15., No. 6, 200, pp. 3301-3311.

Wolff, R. et al., "Basic Concepts of Optical Measuring of Bone Thickness with IR-Beam", 33rd Annual Conference of the IEEE EMBS, 2011, pp. 405-408.

English language abstract and machine-assisted English language translation for JP 2015-125046 A extracted from espacenet.com database on Jun. 27, 2022, 10 pages.

\* cited by examiner

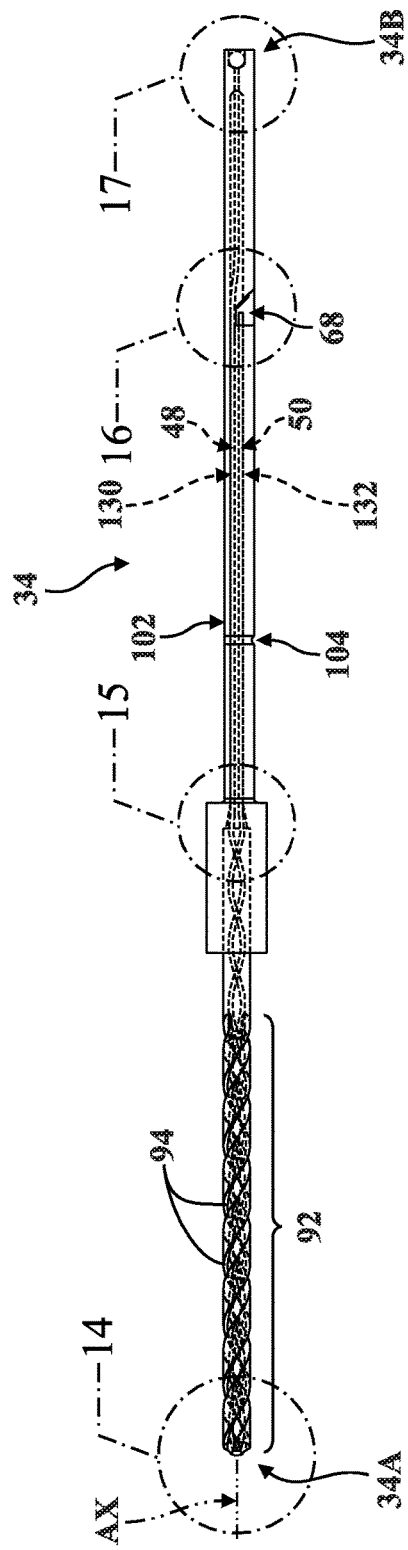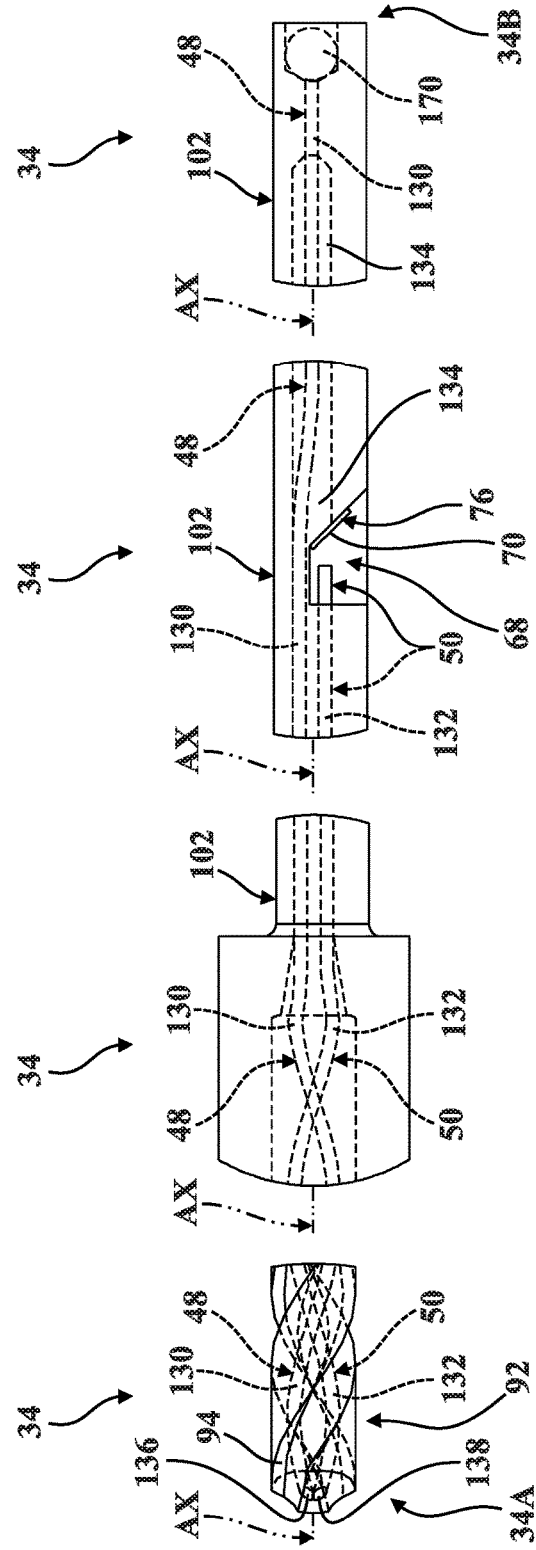

TISSUE PENETRATING SURGICAL SYSTEMS AND METHODS

CROSS-REFERENCE TO RELATED APPLICATION

The subject patent application is the National Stage of International Patent Application No. PCT/IB2018/055874, filed Aug. 3, 2018, which claims priority to and all benefits of U.S. Provisional Patent Application No. 62/541,339, filed Aug. 4, 2017, the disclosure of which is hereby incorporated by reference in its entirety.

TECHNICAL FIELD

The present disclosure relates, generally, to surgical systems and, more specifically, to tissue penetrating surgical systems. The present disclosure also relates to methods of penetrating tissue, detecting boundaries between different tissues, and determining tissue characteristics with surgical systems.

BACKGROUND

Conventional medical and surgical procedures routinely involve the use of surgical tools which allow surgeons to approach and manipulate surgical sites. In particular, rotary instruments such as drills are frequently used in connection with orthopedic procedures to address various musculoskeletal conditions, such as trauma, sports injuries, degenerative diseases, joint reconstruction, and the like. These types of orthopedic procedures routinely involve the use of screws, plates, rods, pins, and other fixation devices to stabilize or articulate bones or fragments thereof. In order to ensure proper installation of fixation devices, the surgeon typically drills a pilot hole into a bone at the surgical site. It is often important for pilot holes, and the fixation device installed therein, not to protrude beyond a maximum depth into the bone or into adjacent tissue.

Most bones of the appendicular and axial skeleton comprise a relatively compact, dense outer bone layer surrounding a relatively porous interior bone layer. Thus, various "tissue boundaries" may be defined between bone layers, as well as by and between other types of tissue, such as bone marrow. In order to ensure that certain tissue boundaries are not traversed during tissue penetration, the surgeon must typically rely on detailed anatomical knowledge, extensive professional experience, and feedback from the rotary instrument (for example, tactile and/or audible feedback). However, it is possible for feedback to occur too late or too rapidly for the surgeon to react before the tissue boundary is traversed.

While conventional tissue penetrating surgical systems have generally performed well for their intended use, there remains a need in the art for addressing one or more of the deficiencies described above.

BRIEF DESCRIPTION OF THE DRAWINGS

Advantages of the embodiments disclosed herein will be readily appreciated as the same becomes better understood after reading the subsequent description taken in connection with the accompanying drawings.

FIG. 13 is a left-side view of the tool body of FIGS. 1A-1B, with internal structural features of the tool body illustrated with dash-dash lines.

FIG. 14 is an enlarged view of a portion of the tool body taken at indicia 14 of FIG. 13.

FIG. 15 is an enlarged view of a portion of the tool body taken at indicia 15 of FIG. 13.

FIG. 16 is an enlarged view of a portion of the tool body taken at indicia 16 of FIG. 13.

FIG. 17 is an enlarged view of a portion of the tool body taken at indicia 17 of FIG. 13.

DETAILED DESCRIPTION OF THE EMBODIMENTS

Figure 1A:
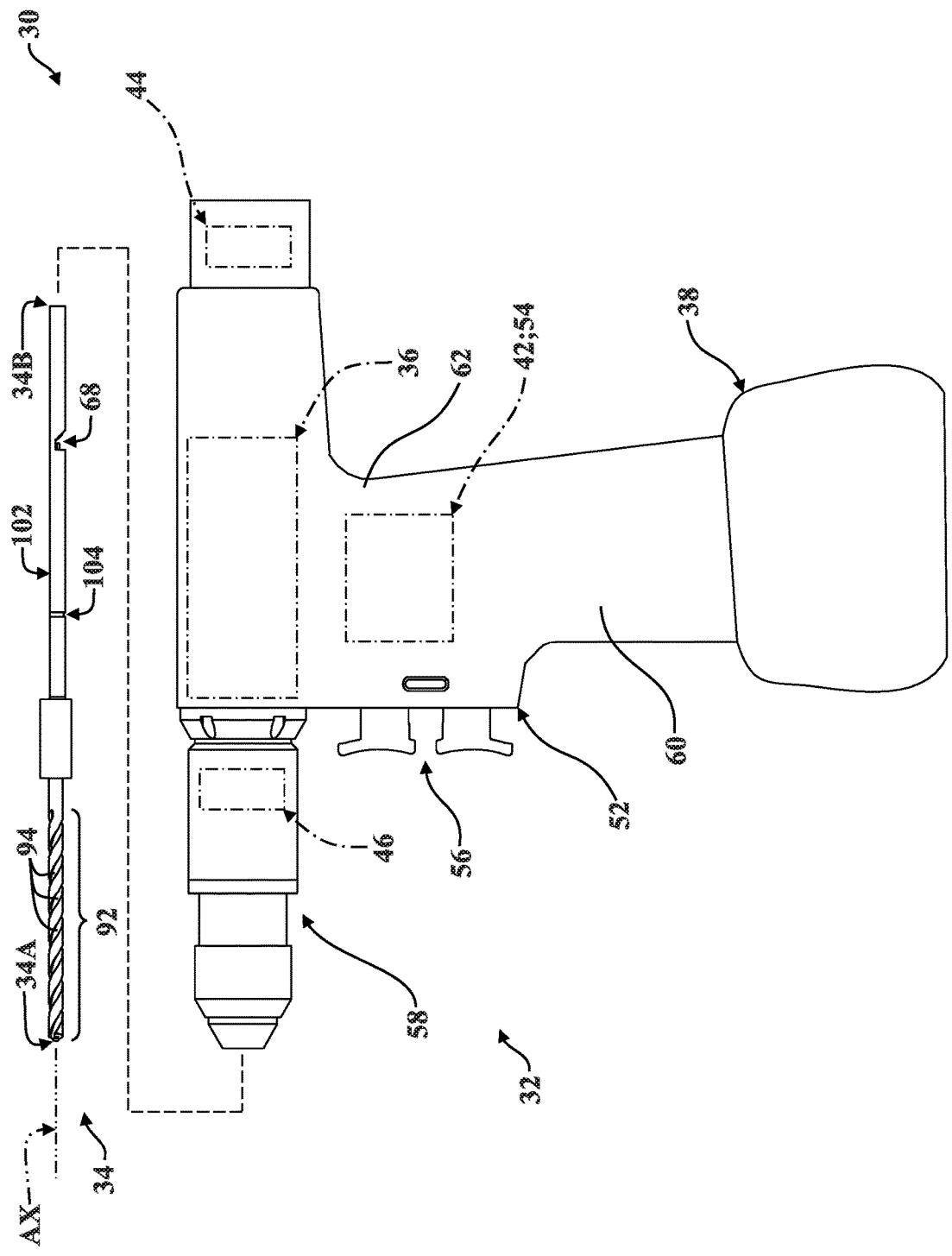
FIG. 1A is schematic view of a tissue penetrating surgical system according to one embodiment, shown with a tool body spaced from a rotary instrument having an emission source and a detector assembly.
Figure 1B:
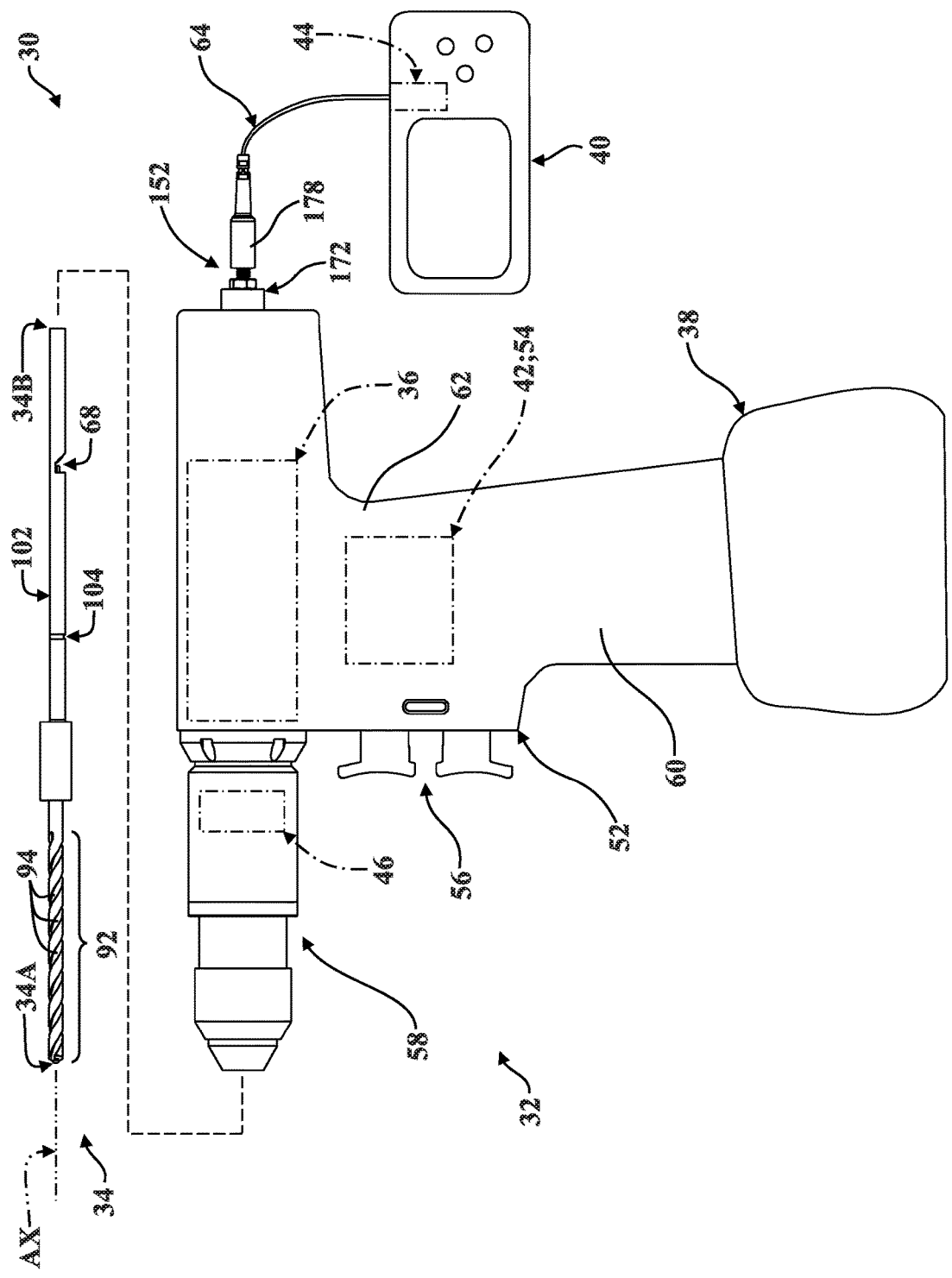
FIG. 1B is a schematic view of a tissue penetrating surgical system according to another embodiment, shown with a tool body spaced from a rotary instrument having a detector assembly and a lightguide extending from the rotary instrument to a console having an emission source.

With reference to the drawings, where like numerals are used to designate like structure throughout the several views, a system is shown for penetrating material of a workpiece and for determining a characteristic of the material. More specifically, a surgical system 30 is shown at 30 in FIGS. 1A-2B for penetrating tissue T of a patient and for determining a characteristic of the tissue T. Thus, in the illustrated embodiments described herein, the workpiece is realized as one or more portions of the patient's anatomy, and the material is realized as one or more types of tissue T. Accordingly, unless otherwise noted, the words "workpiece" and "patient" may be used interchangeably herein, and the words "material" and "tissue" may similarly be used interchangeably herein.

The surgical system 30 generally comprises a rotary instrument 32 to generate rotational torque, and a tool body 34 which is configured to releasably couple to the rotary instrument 32 and to engage tissue T. In the representative embodiment illustrated herein, the rotary instrument 32 is realized as a hand-held drill with an electric motor 36 powered via a rechargeable battery 38, and the tool body 34 is realized as or otherwise forms part of a "drill bit" which extends along an axis AX between a "cutting" distal end 34A to engage tissue T, and a "coupling" proximal end 34B to releasably couple to the rotary instrument 32. Thus, stored electrical energy in the battery 38 powers the motor 36 which, in turn, generates rotational torque to rotate the tool body 34. While the representative embodiment of the rotary instrument 32 illustrated herein employs an "on-board" motor 36 and detachable battery 38, as will be appreciated from the subsequent description below, the components of the surgical system 30 may be configured in a number of different ways, such as where the rotary instrument 32 is tethered to an external console 40 (see FIG. 1B) configured to control, power, or otherwise translate rotational torque to the rotary instrument to facilitate rotating the tool body 34 during use. Conversely, the rotary instrument 32 could be implemented as a portable, untethered instrument with embedded electronics (see FIG. 1A), and could communicate with other external systems, controllers, and the like via various types of wireless communication. Other configurations are contemplated.

Figure 3A:
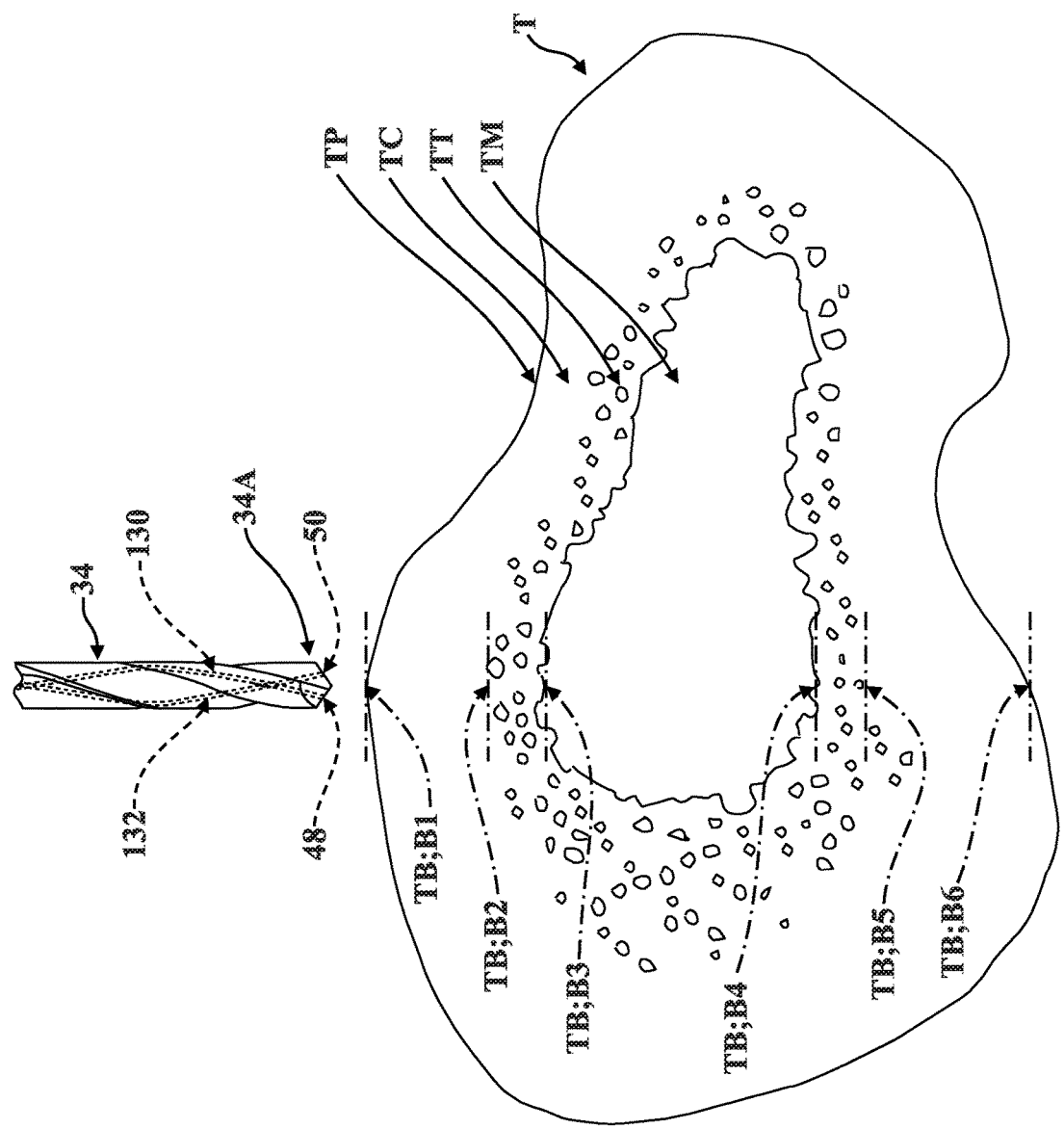
FIG. 3A is a schematic view of the cutting end of the tool body of FIGS. 2A-2B shown positioned adjacent to bone.
Figure 3B:
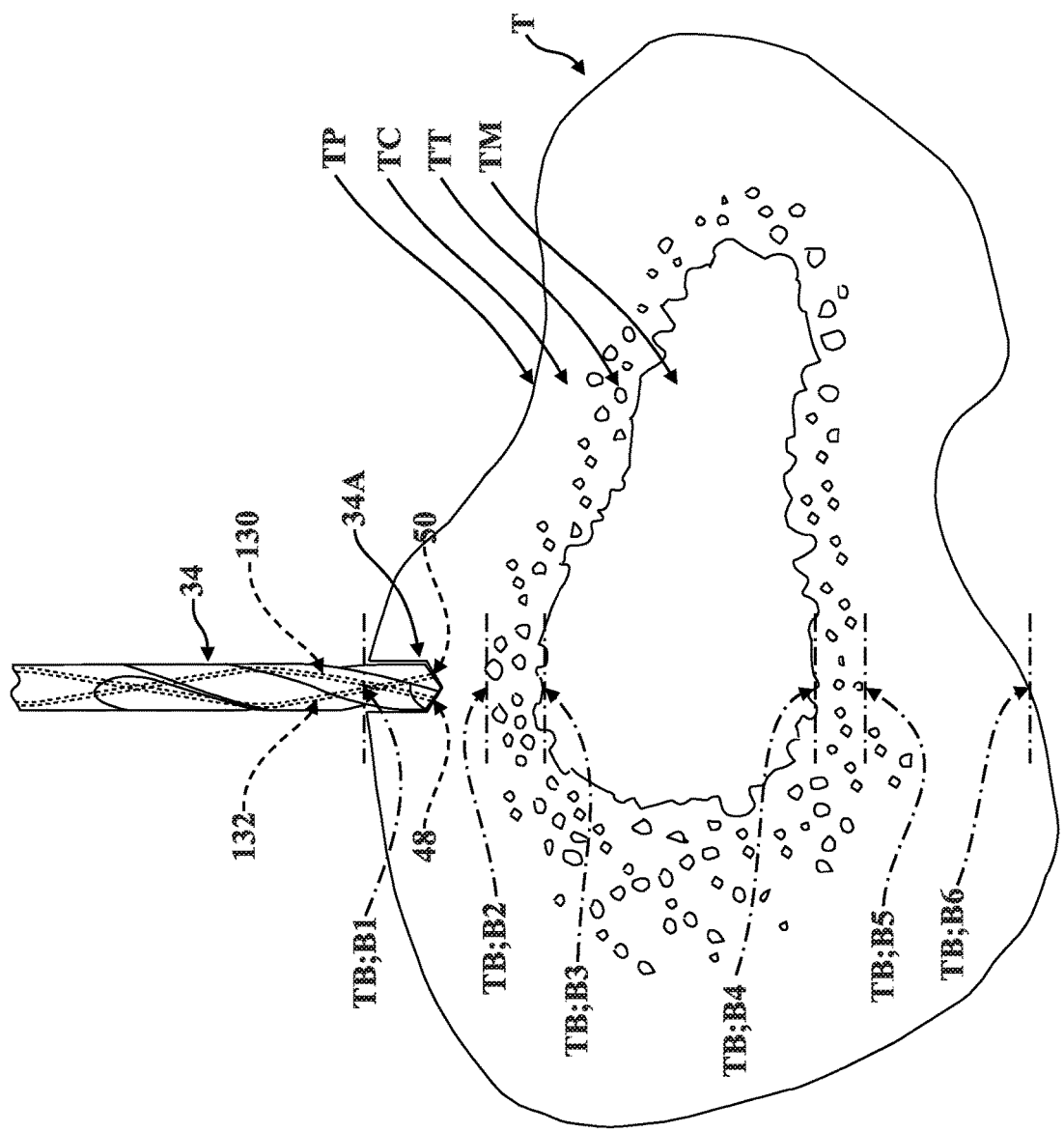
FIG. 3B is another schematic view of the tool body of FIG. 3A, shown with the cutting end penetrating cortical bone and approaching cancellous bone.
Figure 3C:
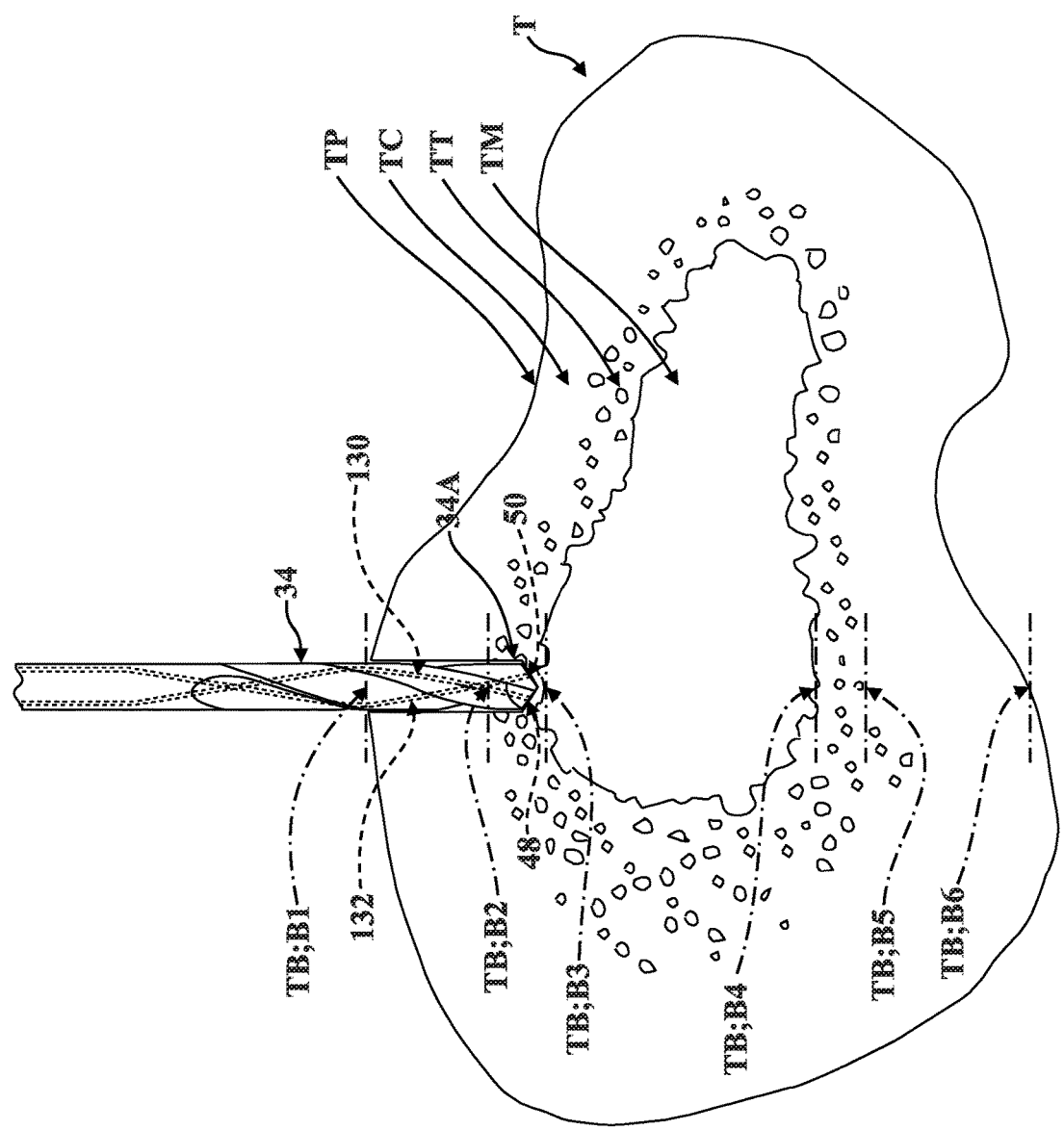
FIG. 3C is another schematic view of the tool body of FIGS. 3A-3B, shown with the cutting end penetrating cancellous bone and approaching marrow.
Figure 3D:
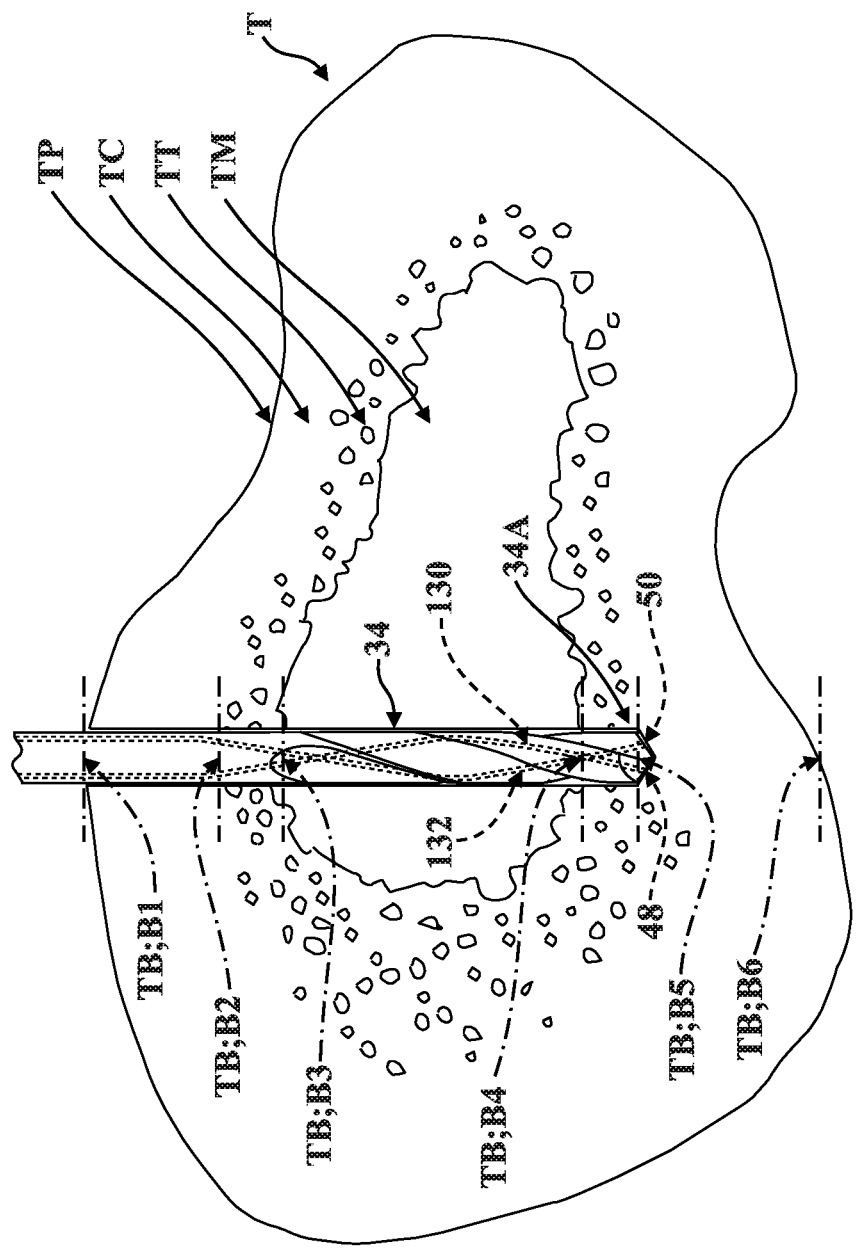
FIG. 3D is another schematic view of the tool body of FIGS. 3A-3C, shown with the cutting end penetrating cancellous bone and approaching cortical bone after having traversed the marrow.

Those having ordinary skill in the art will appreciate that a number of different types of medical and surgical procedures routinely involve "drilling" into tissue T comprising bone, marrow, muscle, nerve, epithelial, and/or connective tissue. For example, reconstructive orthopedic procedures typically require a user, such as a surgeon, to drill into a fractured bone at various locations adjacent to the fracture to install fixation devices which help stabilize the fracture and promote bone redemonstration. Here, the specific depth that the bone needs to be penetrated to can vary significantly based on the type of bone being drilled, the location of the fracture, the patient's anatomical structure, the severity of the fracture, the type of fixation device being utilized, the type of procedure being performed, and the like. By way of illustrative example, FIGS. 3A-3D schematically depict, in section, the distal end 34A of the tool body 34 approaching and/or penetrating a bone. The illustrated bone comprises four different types of tissue T: an outer layer of periosteum TP, a layer of relatively dense cortical bone TC, a layer of relatively porous (or, "cancellous") trabecular bone TT, and bone marrow TM. FIG. 3A shows the distal end 34A positioned adjacent to the outer layer of periosteum TB. FIG. 3B shows the distal end 34A penetrated through the periosteum TB and into the cortical bone TC. FIG. 3C shows the distal end 34A penetrated further into the bone, through the cortical bone TC and into the trabecular bone TT. FIG. 3D shows the distal end 34A penetrated even further into the bone, through the marrow TM and into the trabecular bone TT positioned below the marrow TM.

As will be appreciated from the subsequent description below, the respective positions (or "drilling depths") of the distal end 34A of the tool body 34 shown in FIGS. 3A-3D demonstrate that the process of drilling into tissue T such as bone often involves sequentially penetrating different types of tissue T. Thus, depending on the type of procedure being performed, penetrating to a desired depth may involve traversing one or more tissue boundaries TB defined between adjacent types of tissue T. By way of illustration, the bone depicted in FIGS. 3A-3D defines six boundaries: a first boundary B1 defined between the periosteum TP and the cortical bone TC, a second boundary B2 defined between the cortical bone TC and the trabecular bone TT, a third boundary B3 defined between the trabecular bone TT and the marrow TM, a fourth boundary B4 defined between the marrow TM and the trabecular bone TT, a fifth boundary B5 defined between the trabecular bone TT and the cortical bone TC, and a sixth boundary B6 defined between the cortical bone TC and the periosteum TP. It should be appreciated that different patients may have different bones/anatomies and, as such, the presence of the tissue boundaries TB and/or types of tissue T may not exist for certain patients at certain anatomical sites.

Because each type of tissue T depicted in FIGS. 3A-3D has different physical and material properties, such as hardness, thickness, and the like, each of which may vary between different patients, conventional surgical drilling typically necessitates that the surgeon adjust the amount of axial force exerted on the rotary instrument 32 to compensate for differences in adjacent types of tissue T. By way of illustration, drilling through cortical bone TC (see FIG. 3B) generally requires more axial force compared to drilling through trabecular bone TT (see FIG. 3C). Put differently, if the amount of axial force exerted on the rotary instrument 32 is substantially constant while drilling sequentially through cortical bone TC and periosteum TP, the distal end 34A of the tool body 34 may "plunge" quickly and un an uncontrolled fashion through periosteum TP and into adjacent tissue T, muscle, and the like, after crossing the sixth boundary B6 defined between the cortical bone TC and the periosteum TP. It will be appreciated that this undesirable effect may lead to damaged tissue T and may complicate the remainder of the surgical procedure.

The surgical system 30 of the present disclosure is configured to help prevent excessive tissue T penetration, such as the "plunging" effect described above, by determining characteristics of tissue T which can be used to anticipate tissue boundaries TB during tissue T penetration and, in some embodiments, interrupt penetration before the tissue boundary TB is reached. To this end, and as is depicted schematically in FIGS. 1A-2B, the surgical system 30 employs a controller, generally indicated at 42, an emission source 44, and a detector assembly 46 to determine tissue T properties and detect approaching tissue boundaries TB based on the principles of diffuse reflectance, as described in greater detail below.

The controller 42 is disposed in communication with the rotary instrument 32, the emission source 44, and the detector assembly 46, such as by wired or wireless communication, and is configured to, among other things, drive the emission source 44 and record data from the detector assembly 46. The emission source 44 is operatively coupled to the rotary instrument 32 to emit light toward the tissue T, and the detector assembly 46 is operatively coupled to the rotary instrument 32 to detect light reflected by the tissue T.

Figure 2A:
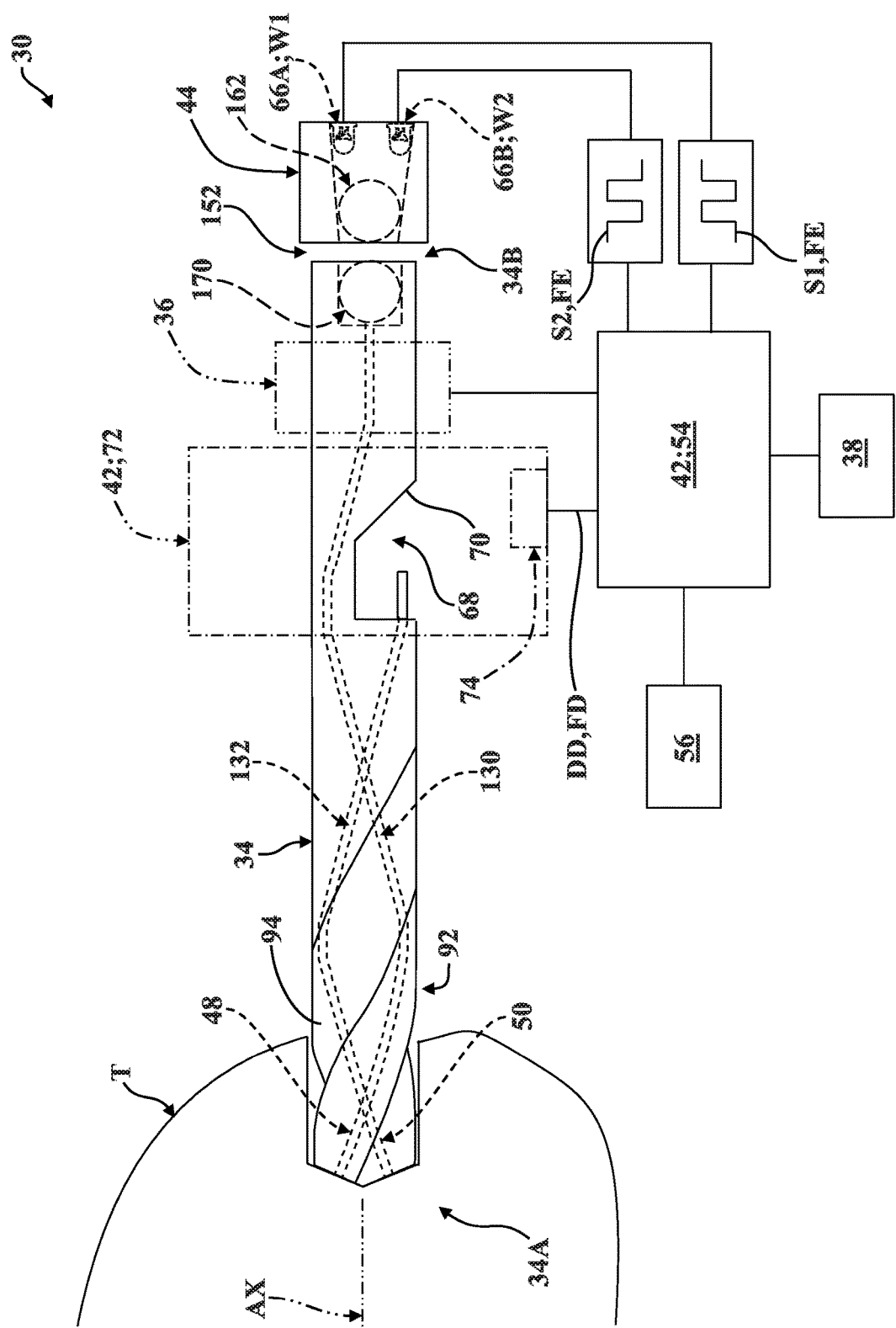
FIG. 2A is a partial schematic view of a controller of the surgical system of FIGS. 1A-1B, shown with a distal cutting end of the tool body penetrating bone.

In order to emit and collect light adjacent to the tissue T during use, an emission lightguide 48 and a detection lightguide 50 are each supported within the tool body 34 to transmit light (see FIG. 2A; lightguides depicted with dashed lines). More specifically, the emission lightguide 48 is disposed in optical communication with the emission source 44 when the tool body 34 is coupled to the rotary instrument 32 to transmit light emitted by the emission source 44 through the emission lightguide 48 and toward the tissue T as the rotary instrument 32 rotates the tool body 34 during use. The detection lightguide 50 is spaced from the emission lightguide 48 and is disposed in optical communication with the detector assembly 46 when the tool body 34 is coupled to the rotary instrument 32 to transmit light reflected by the tissue T through the detection lightguide 50 and toward the detector assembly 46 as the rotary instrument 32 rotates the tool body 34. In some embodiments, the tool body 34, the emission lightguide 48, and the detection lightguide 50 cooperate to define a drill bit that is releasably attachable to the chuck assembly 58, as described in greater detail below.

Figure 2B:
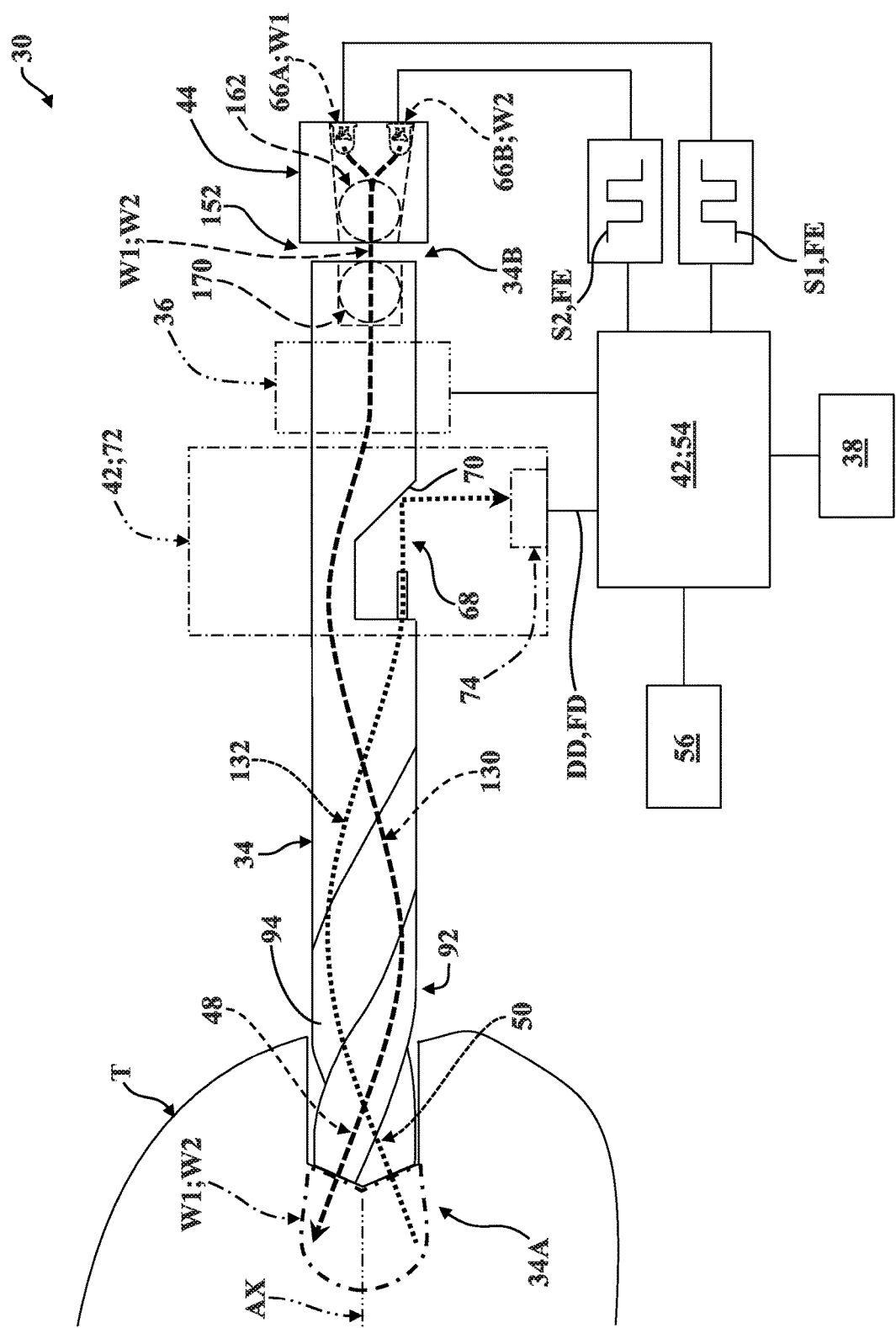
FIG. 2B is another schematic view of the controller of FIG. 2A, shown with two emission sources emitting light axially into a proximal end of the tool body, the emitted light shown directed along an emission lightguide toward the bone, with light reflected by the bone shown directed along a detection lightguide away from the bone and toward the detector assembly.

As is best depicted in FIG. 2B, the emission source 44 emits light into the emission lightguide 48 along the axis AX defined by the tool body 34, and the detector assembly 46 is arranged to detect light that has been reflected from the tissue T and which exits the detection lightguide 50 in a direction transverse to the axis AX when the tool body 34 is coupled to the rotary instrument 32. Put differently, light emitted by the emission source 44, which is represented by a dash-dash line in FIG. 2B, enters the emission lightguide 48 adjacent the proximal end 34B and exits the emission lightguide 48 adjacent the distal end 34A to be absorbed and reflected by tissue T. Conversely, light reflected by the tissue T, which is represented by a dot-dot line in FIG. 2B, enters the detection lightguide 50 adjacent the distal end 34A and exits the detection lightguide 50 in a direction which is transverse to the axis AX to be detected by the detector assembly 46 at a location arranged between the distal end 34A and the proximal end 34B. It will be appreciated that the term "transverse" as used herein means "across" or "intersecting" the axis AX. This configuration allows for "continuous" emission and detection of light during rotation of the tool body 34 along separate lightguides 48, 50 to detect approaching tissue boundaries TB based on predetermined changes in the amount of light absorbed and reflected by the tissue T during penetration.

As will be appreciated from the subsequent description below, while the illustrated surgical system 30 is configured such that light enters the emission lightguide 48 generally "parallel" or otherwise aligned to the axis AX at the proximal end 34B, and travels generally along the axis AX to the distal end 34A; and reflected light enters the detection lightguide 50 at the distal end 34A and travels generally along the axis AX toward the proximal end 34B before exiting the detection lightguide 50 in a direction "perpendicular" or otherwise transverse to the axis AX, the "continuous" detection and emission noted above and described in greater detail below could similarly be achieved by interchanging this arrangement. More specifically, light could be emitted transverse to the axis AX and travel toward the distal end 34A, and reflected light could travel from the distal end 34A to the proximal end 34B. Other configurations are contemplated. By way of non-limiting example, in some embodiments, light could be emitted into and out of the tool body 34 at the proximal end 34B substantially parallel to the axis AX (not shown), or light could be emitted into and out of the tool body transverse to the axis AX (not shown). Thus, the various components, structure, and features of the rotary instrument 32, the tool body 34, the controller 42, the emission source 44, the detector assembly 46, the emission lightguide 48, and the detection lightguide 50 will be described in greater detail below.

Referring now to FIGS. 1A-6, as noted above, the rotary instrument 32 is employed in performing surgical procedures and is powered via the battery 38. While the representative embodiment of the rotary instrument 32 illustrated herein is realized as a hand-held surgical drill, it will be appreciated that the rotary instrument 32 can be of any suitable type or configuration sufficient to penetrate tissue T. In addition to the motor 36, the rotary instrument 32 generally comprises a handpiece body 52, a handpiece controller 54, an input control 56, and a chuck assembly 58. Each of these components will be described in greater detail below.

The handpiece body 52 of the rotary instrument 32 has a generally pistol-shaped profile with a hand grip 60 and a chassis 62. The hand grip 60 is configured to releasably secure to the rechargeable battery 38 (see FIGS. 1A-1B), such as by correspondingly-shaped interlocking connectors which facilitate electrical contact (not shown, but generally known in the related art). The chassis 62 of the handpiece body 52 supports the chuck assembly 58 which, in turn, is configured to releasably secure the tool body 34, as described in greater detail below. Because the rotary instrument 32 is illustrated generically throughout the drawings, those having ordinary skill in the art will appreciate that the specific configuration of the hand grip 60 and/or the chassis 62 could be adjusted to accommodate different applications, different types of rotary instruments 32, and the like.

The handpiece controller 54 of the rotary instrument 32 is disposed in electrical communication with the motor 36, the battery 38, and the input control 56 (see FIGS. 1A-2B), and is generally configured to facilitate operation of the motor 36 in response to actuation of the input control 56. As will be appreciated from the subsequent description below, the handpiece controller 54 could also serve as or otherwise define the controller 42 of the surgical system 30 in some embodiments and, thus, could also be disposed in electrical communication with the emission source 44 and the detector assembly 46. Conversely, the handpiece controller 54 and the controller 42 could be realized as discrete components which communicate with each other. Other configurations are contemplated.

The handpiece controller 54 and the input control 56 of the rotary instrument 32 are each supported within the handpiece body 52. The input control 56 has a trigger-style configuration, is responsive to actuation by the surgeon, and communicates with the handpiece controller 54. The motor 36 is coupled in torque-translating relationship with the chuck assembly 58 and is configured to selectively generate rotational torque in response to commands, signals, and the like received from the handpiece controller 54. Thus, when the surgeon actuates the input control 56 to operate the rotary instrument 32, the handpiece controller 54 directs power from the battery 38 to the motor 36 which, in turn, drives the chuck assembly 58 to rotate the tool body 34. Those having ordinary skill in the art will appreciate that the motor 36, the battery 38, the handpiece body 52, the handpiece controller 54, the input control 56, and the chuck assembly 58 could each be configured in a number of different ways sufficient to facilitate rotating the tool body 34.

As is depicted schematically in FIG. 1A, the emission source 44 and the detector assembly 46, like the battery 38, may advantageously be coupled to the chassis 62 of the rotary instrument 32 for concurrent movement such that the surgical system 30 can be utilized in an "untethered" configuration. However, in other embodiments, the emission source 44 and/or the detector assembly 46 may be situated, positioned, or otherwise arranged differently, such as where the emission source 44 is coupled to the console 40 (see FIG. 1B). Here, optical communication between the rotary instrument 32 and the console 40 can be achieved with an optical tether, generally indicated at 64, configured to direct light from the emission source 44 into the emission lightguide 48 of the tool body 34 when the tool body 34 is coupled to the rotary instrument 32. Thus, those having ordinary skill in the art will appreciate that the emission source 44 and/or the detector assembly 46 can be arranged, disposed, or otherwise configured in any suitable way sufficient to facilitate optical communication with the lightguides 48, 50.

As noted above, the emission source 44 is configured to emit light that is guided along the emission lightguide 48 toward the tissue T to detect tissue boundaries TB during penetration. As will be appreciated from the subsequent description below, the surgical system 30 is configured to direct emitted light into the tissue T "ahead" or "below" the distal end 34A of the tool body 34 to detect approaching tissue boundaries TB during tissue T penetration via diffuse reflectance. Here, because different types of tissue T absorb and reflect light in different ways, and because emitted light is directed out of the distal end 34A, the amount of light reflected and absorbed by the tissue T changes depending on the type of tissue T being penetrated and, thus, also changes as the distal end 34A approaches a tissue boundary TB.

Referring now to FIGS. 2A-2B, the representative embodiment of the emission source 44 comprises a first light source 66A and a second light source 66B. The first light source 66A is arranged to emit light into the emission lightguide 48 at a first wavelength W1. The second light source 66B is likewise arranged to emit light into the emission lightguide 48, but emits light at a second wavelength W2 which is different from the first wavelength W1. In some embodiments, the light sources 66A, 66B comprise respective light emitting diodes (LEDs) which are driven by the controller 42 to emit light. However, it will be appreciated that the light sources 66A, 66B could be of any suitable type or configuration sufficient to emit light directed into the emission lightguide 48. By way of non-limiting example, it is conceivable that the light sources 66A, 66B could each comprise respective laser diodes, could be defined by a single LED with a common anode or cathode, and the like. Similarly, while two LEDs are depicted schematically in FIGS. 2A-2B, it will be appreciated that the light sources 66A, 66B could be of different types, configurations, sizes, and the like, and a single light source could be employed to emit light at one wavelength or at different wavelengths. Furthermore, the light sources 66A, 66B could be arranged or otherwise supported in any suitable way sufficient to emit light into the emission lightguide 48.

With continued reference to FIGS. 2A-2B, the controller 42 is disposed in electrical communication with the light sources 66A, 66B and is configured to asynchronously drive the light sources 66A, 66B to sequentially emit light into the emission lightguide 48 at the first wavelength W1 and at the second wavelength W2. To this end, in the illustrated embodiment, the controller 42 is configured to generate a first square wave S1 to drive the first light source 66A, and to generate a second square wave S2 to drive the second light source 66B. In the illustrated embodiment, the first square wave S1 and the second square wave S2 are 180-degrees out of phase with each other to facilitate asynchronously driving the light sources 66A, 66B. However, it will be appreciated that the controller 42 could drive the first square wave S1 and the second square wave S2 differently. The controller 42 is configured to drive the light sources 66A, 66B at an emission frequency FE, and to acquire detection data DD from the detector assembly 46 over time at a detection frequency FD which is twice the emission frequency FE in the illustrated embodiment. However, it will be appreciated that the controller 42 could be configured to collect the detection data DD from the detector assembly 46 at any frequency suitable to facilitate "continuous" detection. Put differently, the controller 42 acquires detection data DD each time one of the light sources 66A, 66B emits light. In some embodiments, the emission frequency FE is greater than 100 Hz. Other configurations are contemplated.

As will be appreciated from the subsequent description of FIG. 4 below, the light sources 66A, 66B are configured to emit light at different wavelengths W1, W2 to, among other things, help ensure reliable detection of a number of different tissue boundaries TB. To this end, in one embodiment, the first wavelength W1 and the second wavelength W2 are each between 400 nm and 1000 nm. In one embodiment, the first wavelength W1 is between 630 nm and 670 nm and the second wavelength is between 700 nm and 900 nm. However, other configurations are contemplated, and the first wavelength W1 and/or the second wavelength W2 may be selected to accommodate different application requirements, from any suitable wavelength in the visible, near-infrared, and/or infrared light spectrums. Advantageously, the light sources 66A, 66B are configured or otherwise driven such that the first wavelength W1 is absorbable by blood and the second wavelength W2 is less absorbable by blood than the first wavelength W1.

Figure 4:
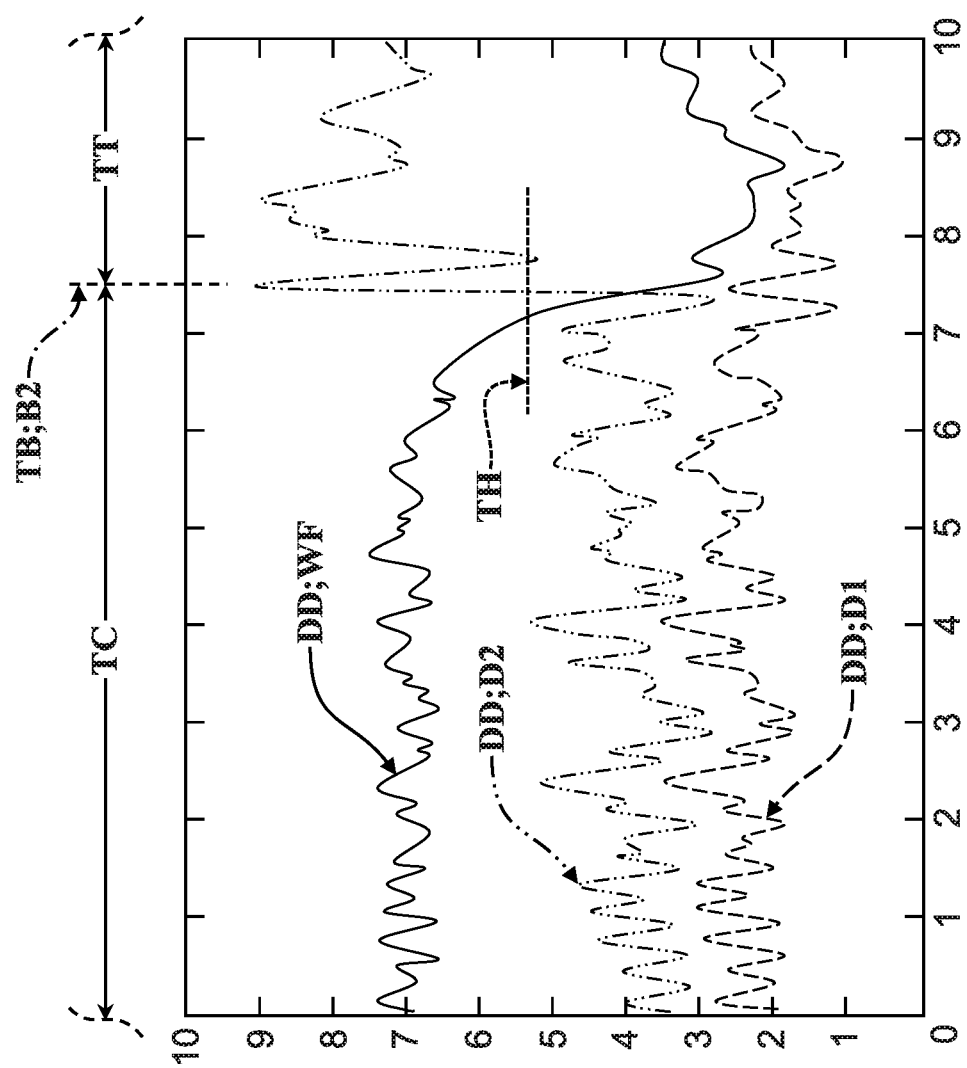
FIG. 4 is a time-based graph depicting first and second diffuse reflectance values measured by the controller of FIGS. 2A-2B, and also depicting a waveform generated based on the diffuse reflectance values.
Figure 5:
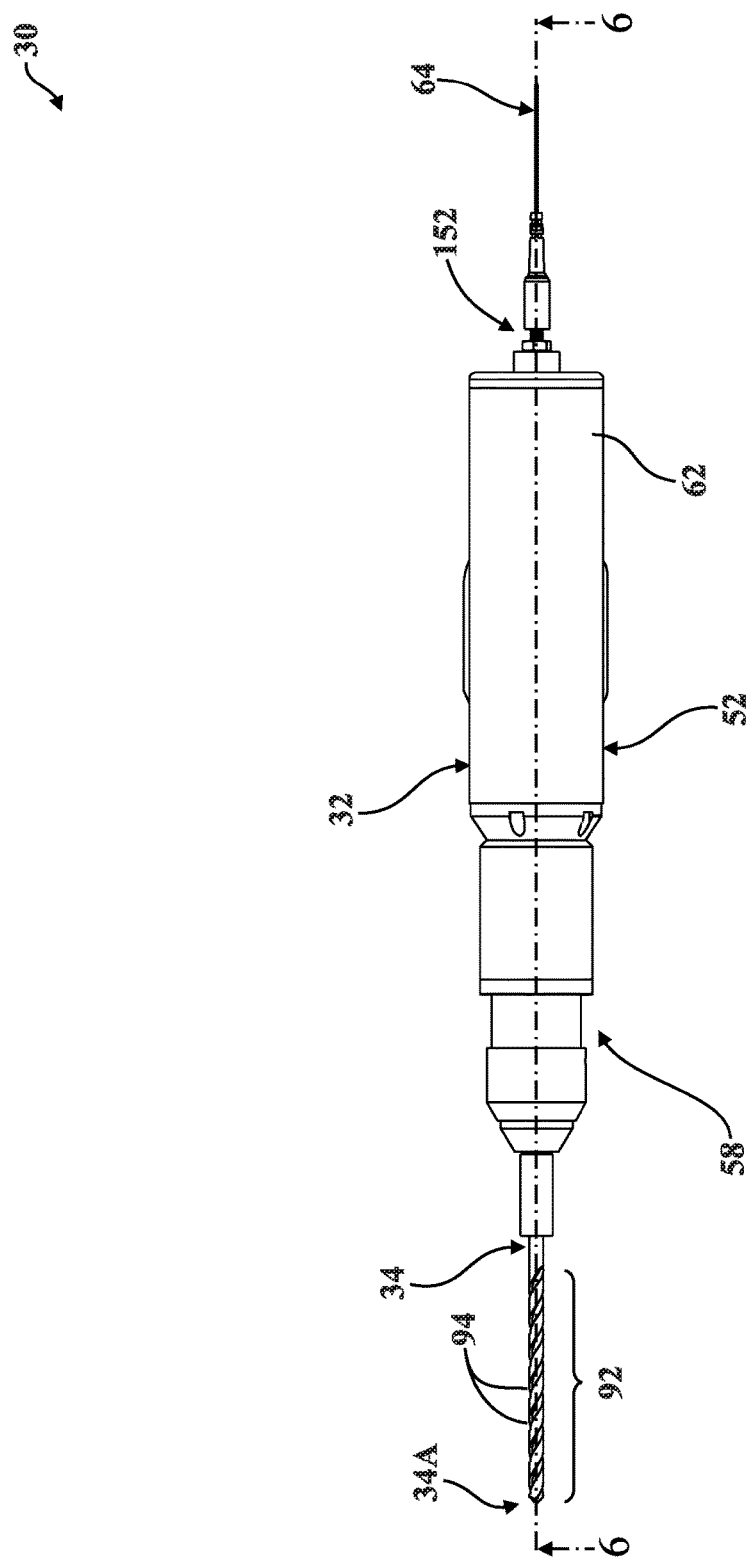
FIG. 5 is a partial top-side view of the surgical system of FIG. 1B, shown with the tool body operatively coupled to the rotary instrument.
Figure 6:
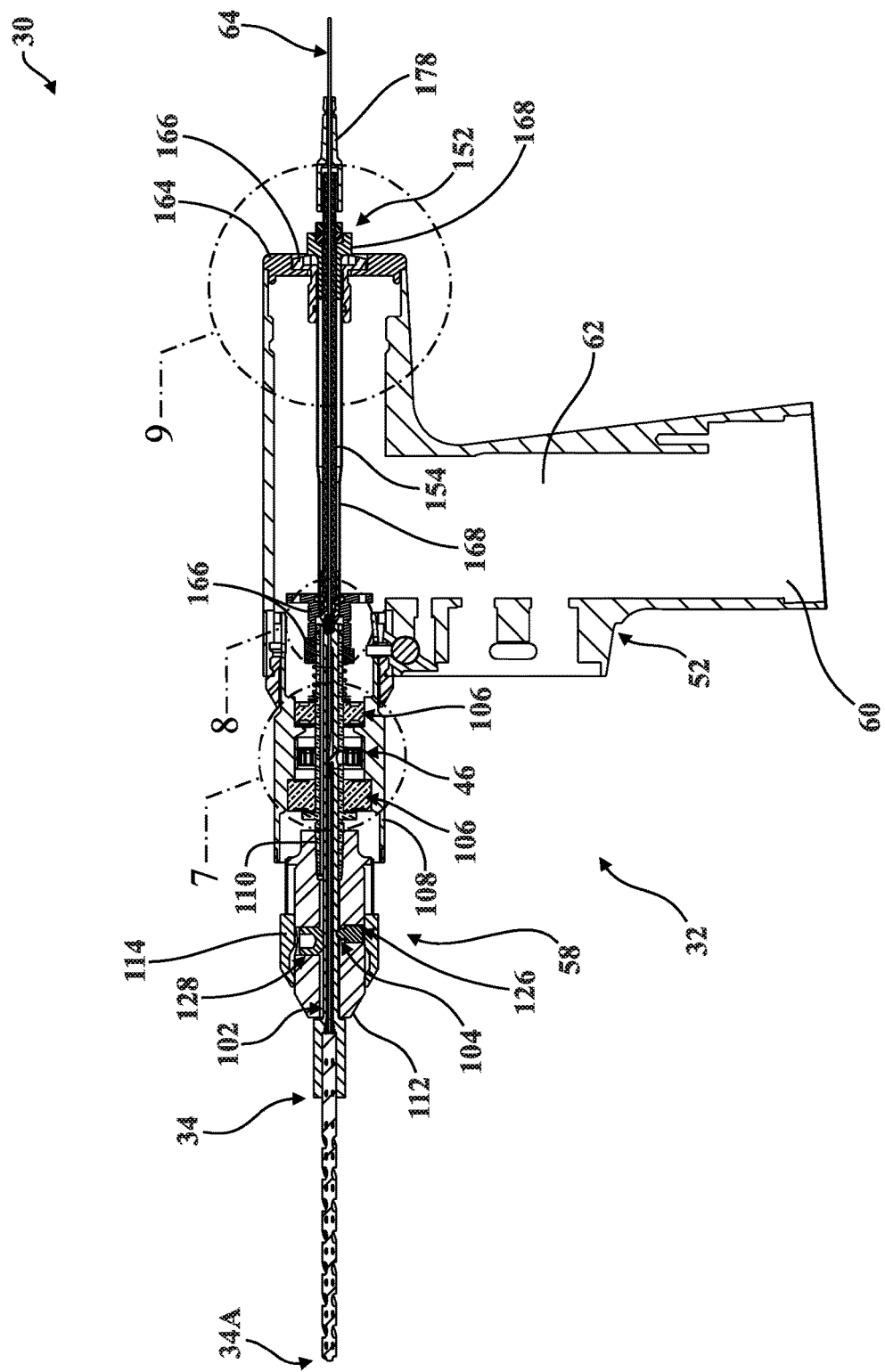
FIG. 6 is a section view taken along line 6-6 of FIG. 5.

Referring now to FIGS. 2A-2B and 4, as noted above, the detector assembly 46 detects reflected light and the controller 42 acquires detection data DD from the detector assembly 46 each time one of the light sources 66A, 66B is respectively driven. Here, detection data DD comprise a first diffuse reflectance value D1 measured with the detector assembly 46 while driving the first light source 66A, and a second diffuse reflectance value D2 measured with the detector assembly 46 while driving the second light source 66B. The controller 42 is also configured to generate a waveform WF based on the first diffuse reflectance value D1 and the second diffuse reflectance value D2, to analyze the waveform WF over time with respect to a tissue boundary threshold TH during tissue T penetration, and to control the rotary instrument 32 in response.

In FIG. 4, a time-based graph is shown depicting lines representing first diffuse reflectance values D1 and second diffuse reflectance values D2 collected during tissue T penetration, and a line representing the waveform WF generated based thereon. To this end, in the illustrated embodiment, the waveform WF is generated as a normalization ratio of the diffuse reflectance values D1, D2. Put differently, the controller 42 is configured to generate the waveform WF based at least partially on a ratio of the first diffuse reflectance value D1 to the second diffuse reflectance value D2, and the controller 42 is configured to analyze the waveform WF during tissue penetration for changes in the ratio occurring over time. Thus, in FIG. 4, the horizontal axis is time and the vertical axis is arbitrary to help clearly depict the waveform WF and the detection data DD for each of the diffuse reflectance values D1, D2 measured over time.

It will be appreciated that utilization of the ratio in generating the waveform WF normalizes the diffuse reflectance values D1, D2 to effectively filter out certain types of "signal noise" present in both diffuse reflectance values D1, D2. However, depending on the specific configuration of the surgical system 30, the accuracy of the detector assembly 46, the speed of the detection and emission, and the like, it is conceivable that the controller 42 could simultaneously monitor for changes in one or both diffuse reflectance values D1, D2 to detect approaching tissue boundaries TB, or could filter noise and/or compare the diffuse reflectance values D1, D2 differently.

The graph illustrated in FIG. 4 represents sequential penetration of two different types of tissue T delineated by a tissue boundary TB to demonstrate how changes in the waveform WF over time and with respect to the tissue boundary threshold TH can be used to interrupt or otherwise control penetration before the tissue boundary TB is traversed. Here in FIG. 4, the waveform WF begins to change significantly with respect to the vertical axis as the tissue T is penetrated over time and as the tissue boundary TB approaches. Thus, once the tissue boundary threshold TH has been exceeded, the controller 42 can interrupt operation of the rotary instrument 32 in response. To this end, the controller 42 could communicate with the handpiece controller 54, and/or with other components of the surgical system 30, to facilitate interruption of penetration. By way of non-limiting illustration, the controller 42 could open a relay disposed between the battery 38 and the motor 36 once to the tissue boundary threshold TH has been exceeded. It will be appreciated that the controller 42 could be configured to completely stop rotation of the tool body 34, slow rotation, and/or provide different types of feedback, such as by illuminating visual indicators, sounding audible alarms, generating haptic feedback, and the like. Other configurations are contemplated. In addition to interrupting rotation of the tool body 34, in some embodiments the controller 42 is configured to determine a patient-specific bone characteristic BC (or, a "workpiece-specific material characteristic") during tissue T penetration in bone. By way of non-limiting illustrations, patient-specific bone characteristics BC may include bone density, hardness, thickness, or other physical parameters of one or more types of tissue T. In some embodiments, detection data DD and/or predetermined patient data such as Electronic Medical Record (EMR) data may also be utilized by the controller 42 to determine the patient-specific bone characteristic BC, adjust the waveform WF, and/or control the rotary instrument 32. Here, for example, the controller 42 may determine that a particular patient's bones have a certain hardness value used to determine or otherwise define a patient-specific bone characteristic BC to control the surgical system 30.

Referring now to FIGS. 5-22, as noted above, the tool body 34 cooperates with the emission lightguide 48 and the detection lightguide 50 to facilitate "continuous" detection and emission of light. To this end, and as is best depicted in FIGS. 7, 16, and 20A-20B, the tool body 34 defines a recess 68 formed transverse to the axis AX and arranged between the distal end 34A and the proximal end 34B with the detection lightguide 50 extending along the tool body 34 from the distal end 34A to the recess 68. A reflector surface 70 is positioned within the recess 68 to direct light transmitted along the detection lightguide 50 toward the detector assembly 46 (see also FIG. 2B). As is described in greater detail below, the detector assembly 46 comprises a brace 72 supporting a plurality of photodetector elements 74 arranged each facing the axis AX to detect light directed from the reflector surface 70 as the rotary instrument 32 rotates the tool body 34 during use (see FIGS. 20A-20B). In the representative embodiment illustrated herein, the detector assembly 46 is provided with twenty photodetector elements 74 which are each configured to sense light and to communicate detection data DD to the controller 42, as noted above. In some embodiments, the photodetector elements 74 are supported on a common "ribbon" or flexible conduit (not shown) which, in turn, is coupled to the brace 72 and is wired to the controller 42.

The brace 72 has a generally annular configuration and helps facilitate alignment of the photodetector elements 74 relative to the axis AX and to the chuck assembly 58. Because the detector assembly 46 is supported by the chuck assembly 58 which, as described in greater detail below, is removable from the chassis 62 of the handpiece body 52, the rotary instrument 32 may comprise electrical contacts (not shown) to facilitate removable electrical connection between the detector assembly 46, the controller 42, and/or the handpiece controller 54. While each of the photodetector elements 74 is supported by the brace 72 in the illustrated embodiment, it is conceivable that all or some of the photodetector elements 74 could be operatively coupled to one or more parts of the rotary instrument 32 without the use of a brace 72. Moreover, those having ordinary skill in the art will appreciate that the photodetector elements 74 could be of a number of different types and/or configurations, and could be arranged, supported, wired, and/or aligned in different ways depending on application requirements, and could communicate with the controller 42 in an suitable way. Furthermore, in certain embodiments, the photodetector elements 74 of the detector assembly 46 are arranged that such that the detector assembly 46 is capable of "continuous" detection, meaning that light reflected by tissue T during penetration can always be detected by one or more of the photodetector elements 74 during rotation of the tool body 34 as tissue T is penetrated. Moreover, while twenty photodetector elements 74 are arranged radially about the brace 72 to achieve "continuous" detection, it will be appreciated that different numbers of photodetector elements 74 could be utilized in certain applications, with or without the use of a discrete brace 72, as noted above. By way of illustrative example, one or more photodetector elements 74 could form part of an "integrating sphere" arrangement, defined such as by a highly-reflective white coating applied within a part of the chuck assembly 58 to reflect light exiting the detection lightguide 50 until captured by the photodetector elements 74 (integrating sphere arrangement not shown).

Figure 7:
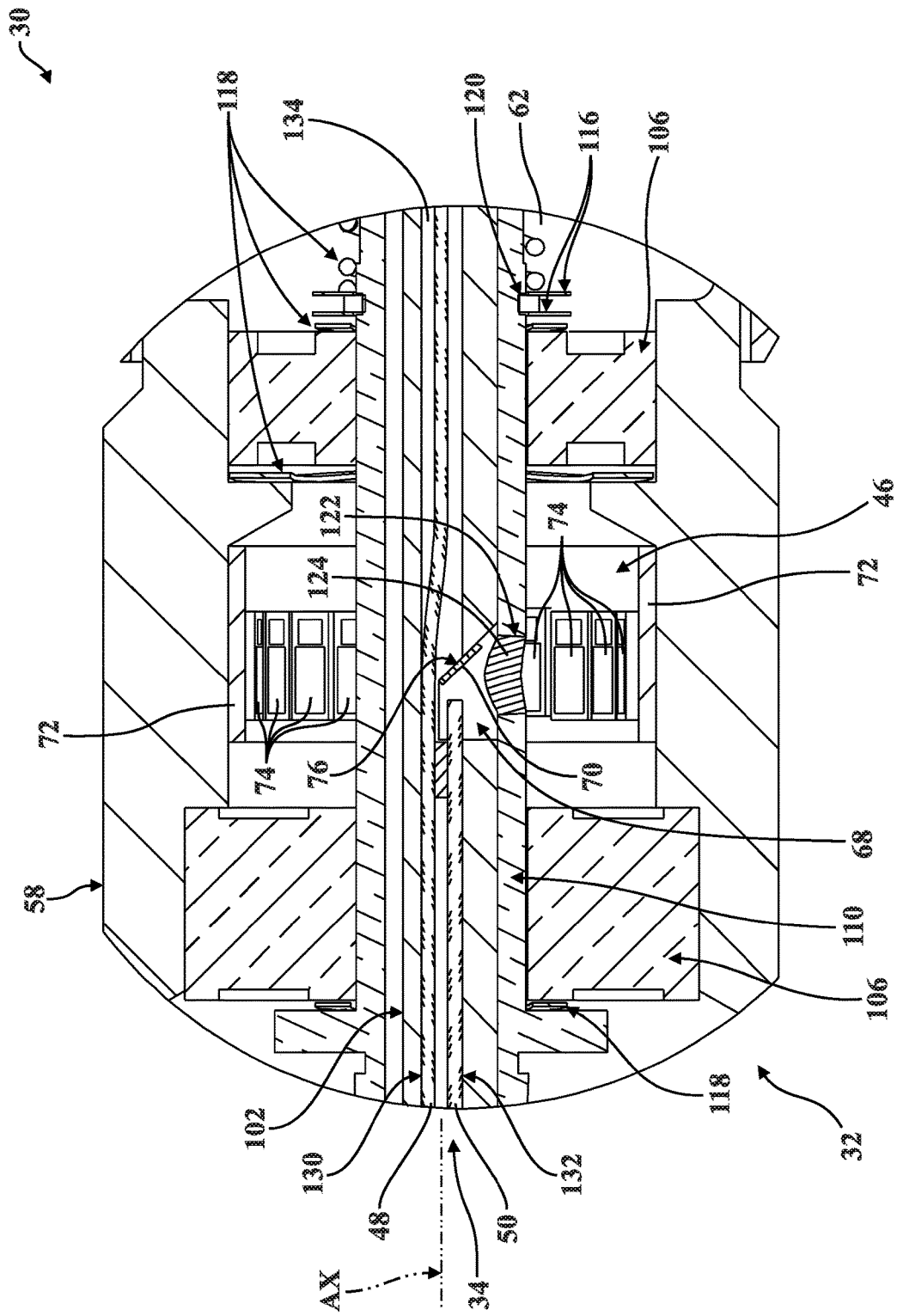
FIG. 7 is a partial section view taken at indicia 7 of FIG. 6.

As shown in FIGS. 7 and 16, the reflector surface 70 is defined by a reflector element 76, such as a mirror, which is supported within the recess 68 of the tool body 34. However, it will be appreciated that the reflector element 76 could be omitted in certain embodiments, such as where the reflector surface 70 is defined by a portion of the tool body 34 itself. In the embodiment illustrated in FIG. 21, an insert 78 defines the reflector surface 70 and is secured to the tool body 34 such as with a press-fit configuration, adhesive, and the like. Adjacent to the insert 78, a cover 80 is provided to help facilitate routing of the lightguides 48, 50 and assembly of the tool body 34. In some embodiments, the reflector surface 70 may be defined by a coating on one or more portions of the tool body 34.

Figure 21:
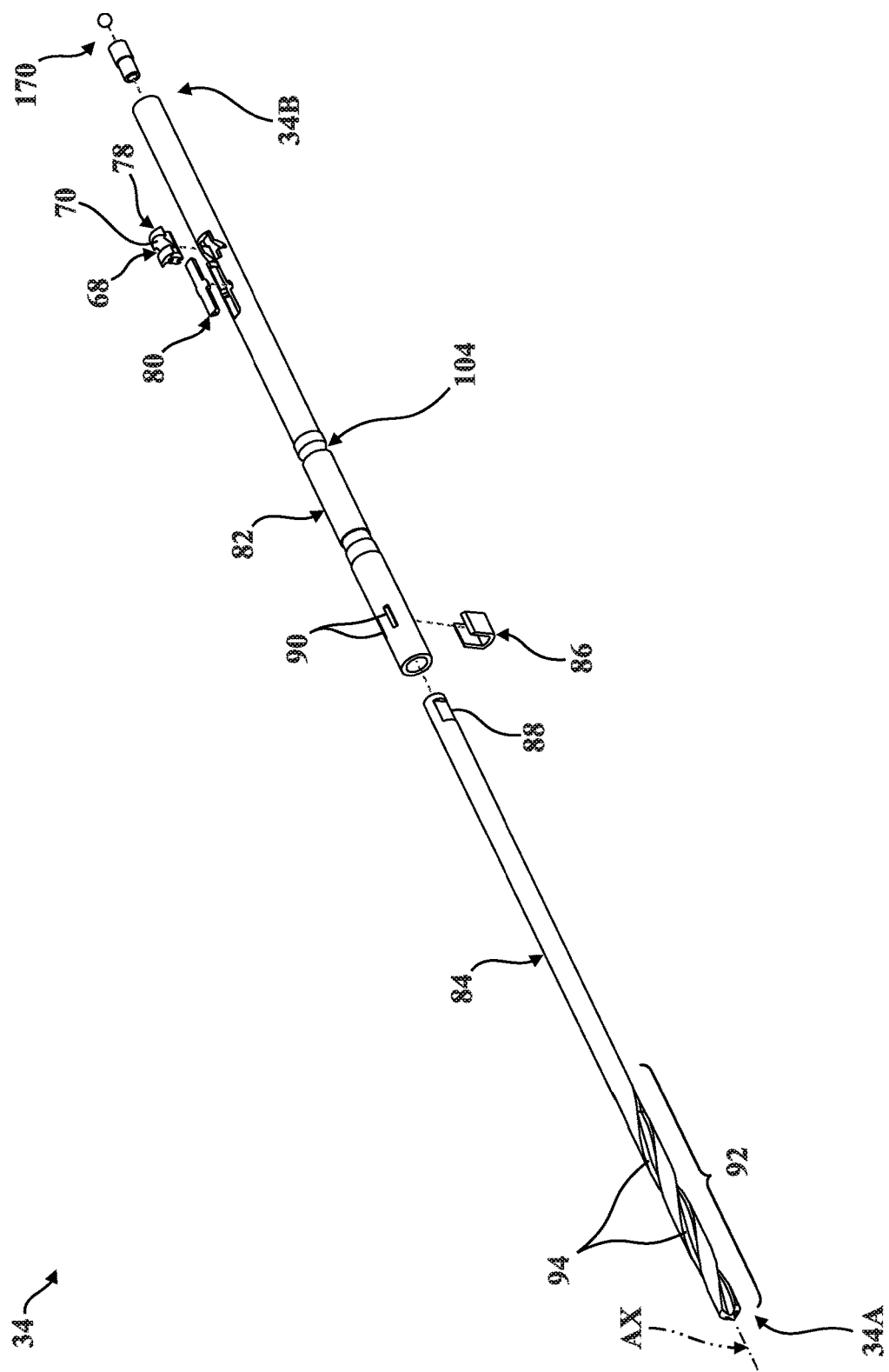
FIG. 21 is an exploded perspective view of a tool body according to another embodiment.

In some embodiments, tool body 34 comprises a shank member 82 and a bit member 84. The shank member 82 is releasably attachable to the chuck assembly 58 and is fixed to the bit member 84 for concurrent rotation. As will be appreciated from the subsequent description below, this configuration helps facilitate manufacture of the tool body 34. However, the tool body 34 could alternately be configured as a unitary, one-piece component. In the embodiment depicted in FIGS. 13-20B, the shank member 82 is fixed to the bit member 84 via a press-fit, interference-fit, or a similar manufacturing process. However, it will be appreciated that the shank member 82 could be secured to the bit member 84 in a number of different ways, such as with welding, adhesives, interlocking structural features, and the like. In the embodiment illustrated in FIG. 21, a clip 86 is provided to retain the shank member 82 to the bit member 84 and to inhibit rotation and axial movement therebetween. To this end, as illustrated by FIG. 21 the clip 86 is configured to abut against shoulders 88 formed in the bit member 84, and to extend into pockets 90 formed in the shank member 82. Other configurations are contemplated.

Figure 19:
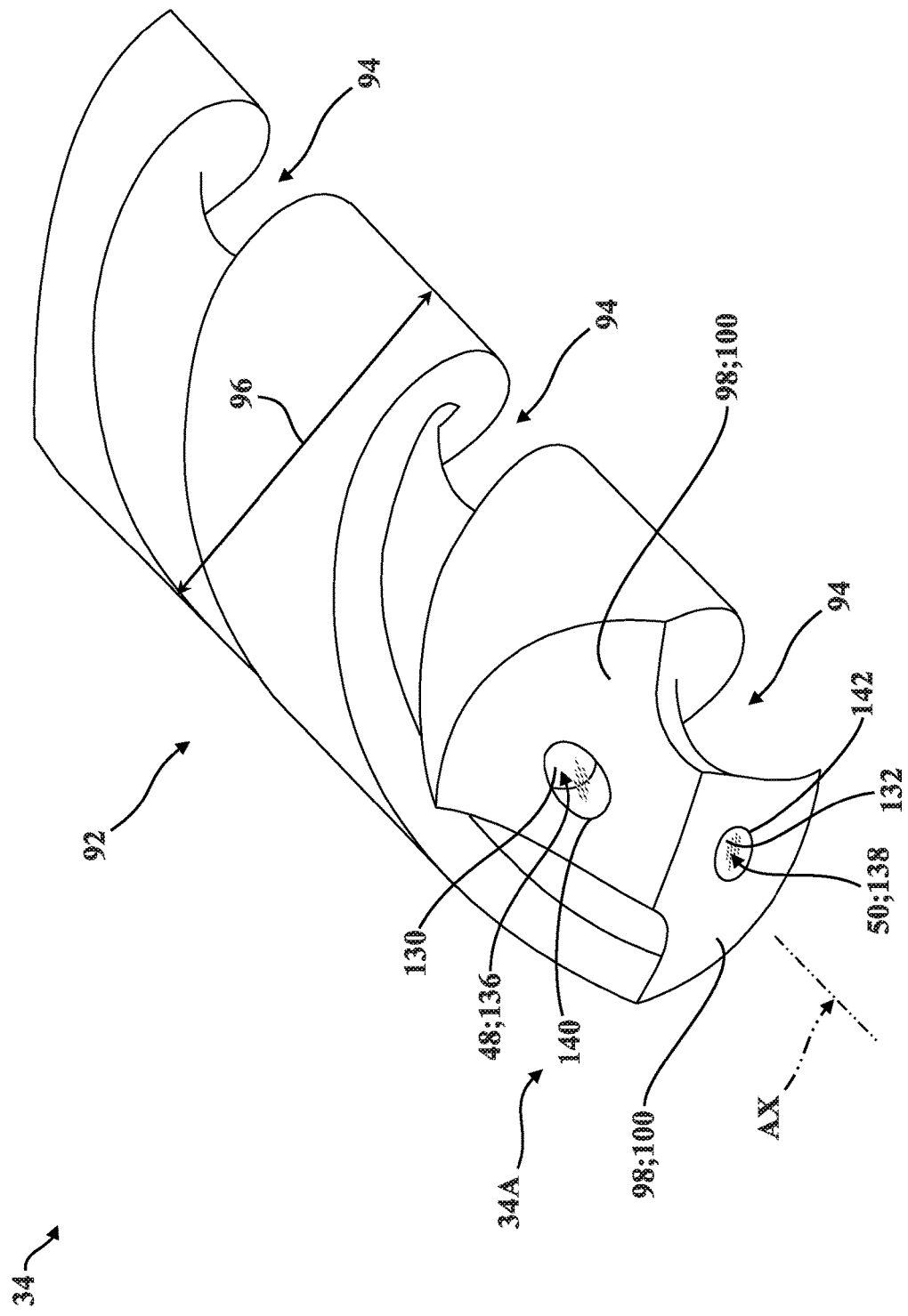
FIG. 19 is a partial perspective view of the distal cutting end of the tool body of FIGS. 13-18.
Figure 20A:
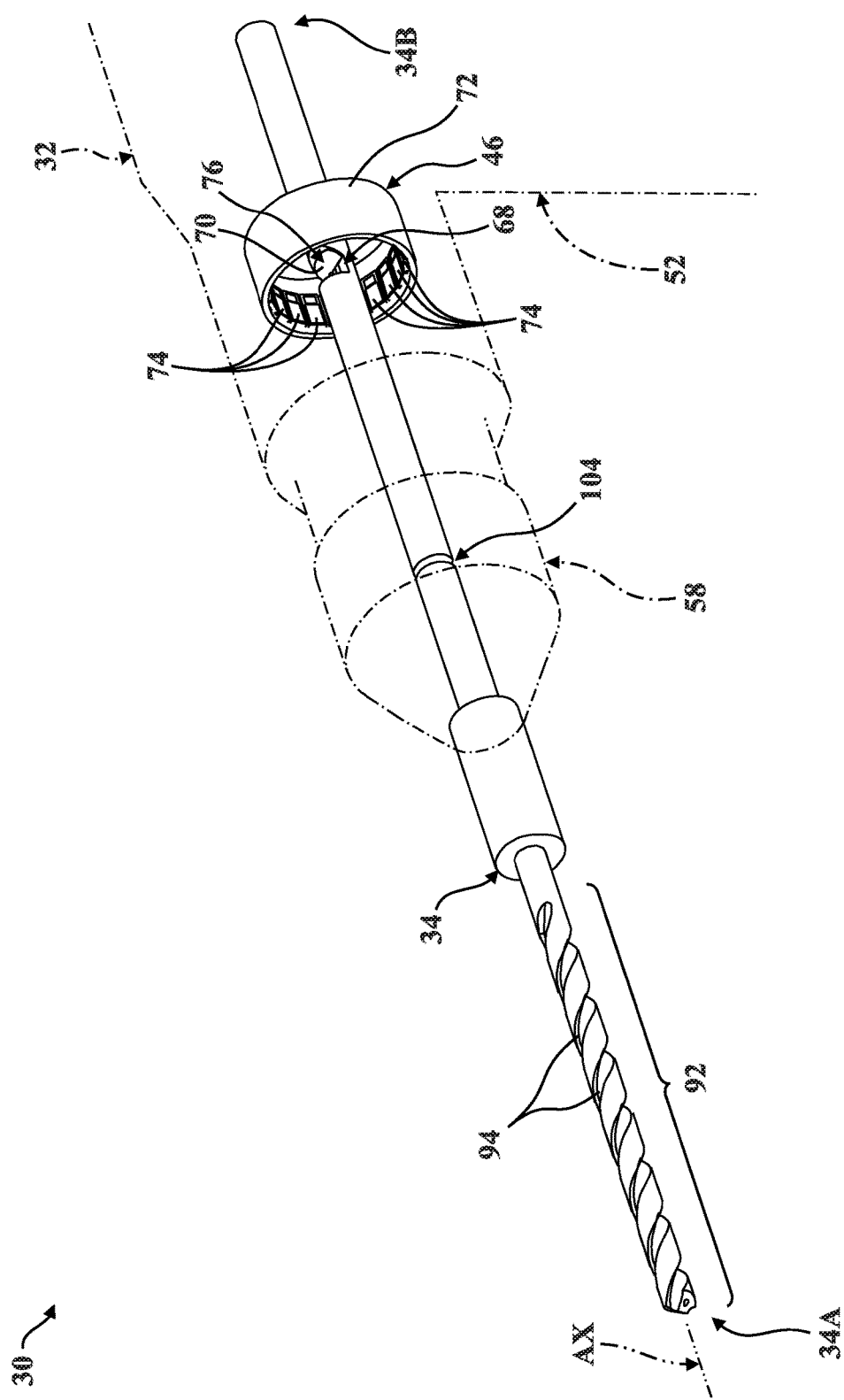
FIG. 20A is a perspective view showing the tool body of FIGS. 1A-1B and 13-19 disposed in one rotational position relative to the detector assembly of FIGS. 1A-2B, with a portion of the handpiece shown in phantom.
Figure 20B:
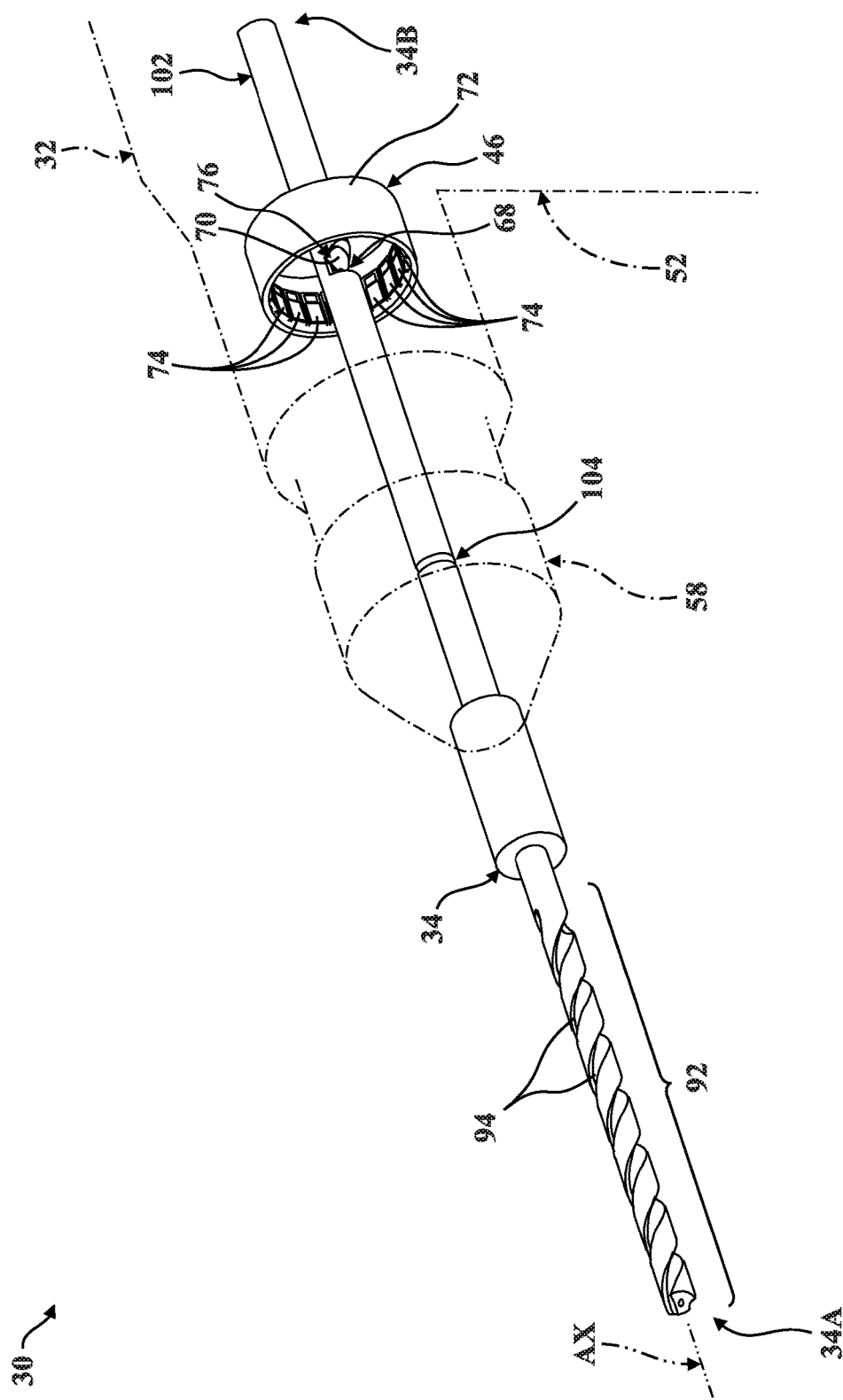
FIG. 20B is another perspective view of the tool body and the detector assembly of FIG. 20B, shown with the tool body disposed in another rotational position relative to the detector assembly.

The bit member 84 of the tool body 34 defines a cutting region 92 adjacent to the distal end 34A which is shaped or otherwise configured to promote tissue T penetration. More specifically, the tool body 34 comprises flutes 94 formed along the cutting region 92 to direct tissue T away from the distal end 34A and toward the proximal end 34B of the tool body 34. It will be appreciated that the flutes 94 could be implemented in a number of different ways, such as with different pitches and shapes (compare FIG. 21 with FIGS. 20A-20B). As is best depicted in FIG. 19, the cutting region 92 of the tool body 34 defines a major drill diameter 96 and comprises a cutting tip face 98 formed at a tip angle 100 (see also FIG. 22) defined between the distal end 34A of the tool body 34 and the portion of the cutting region 92 defining the major drill diameter 96. In one embodiment, the tip angle 100 is between 90-degrees and 130-degrees. However, other configurations are contemplated.

Figure 11:
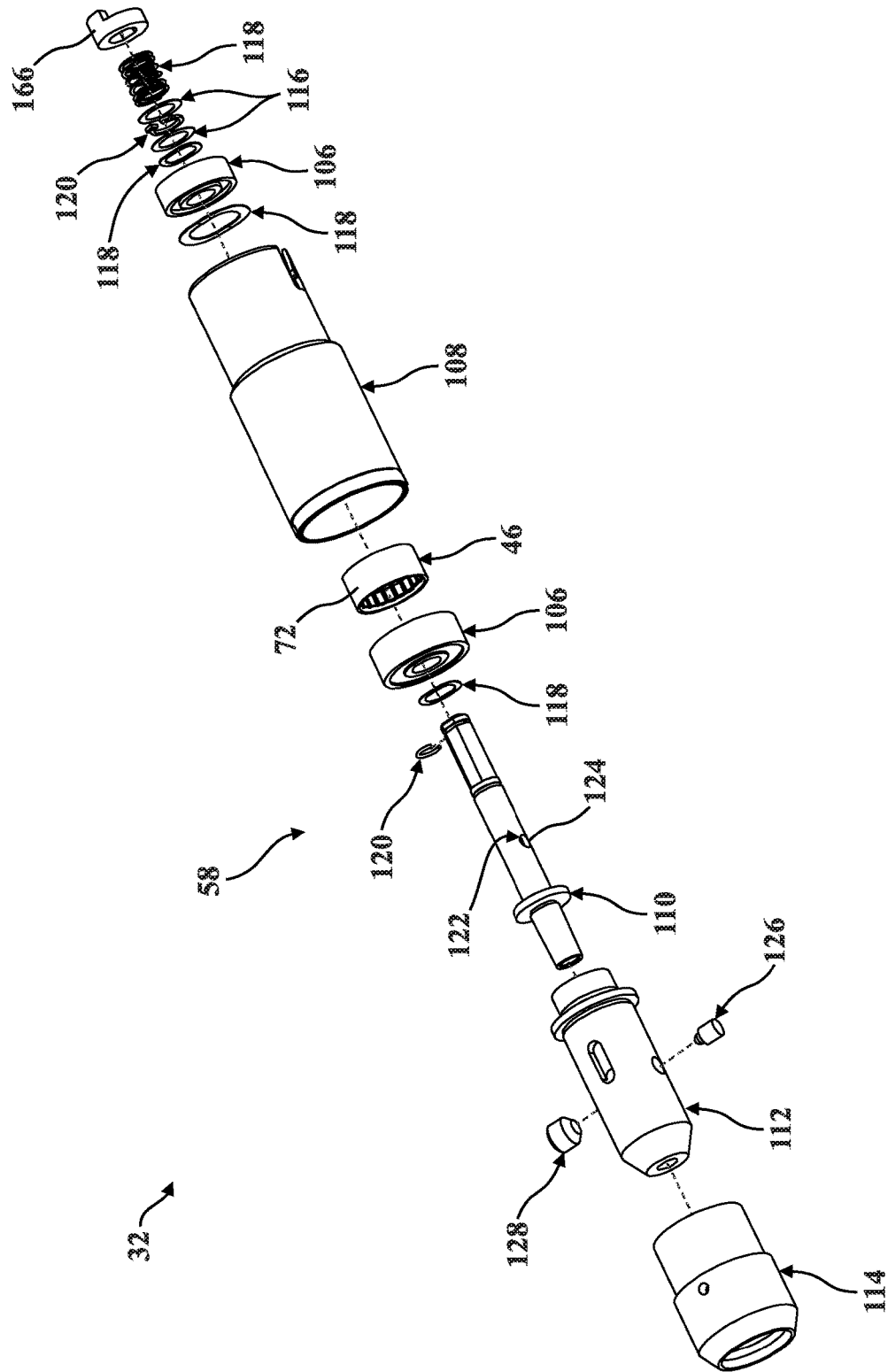
FIG. 11 is an exploded perspective view of the chuck assembly of FIG. 10.
Figure 12:
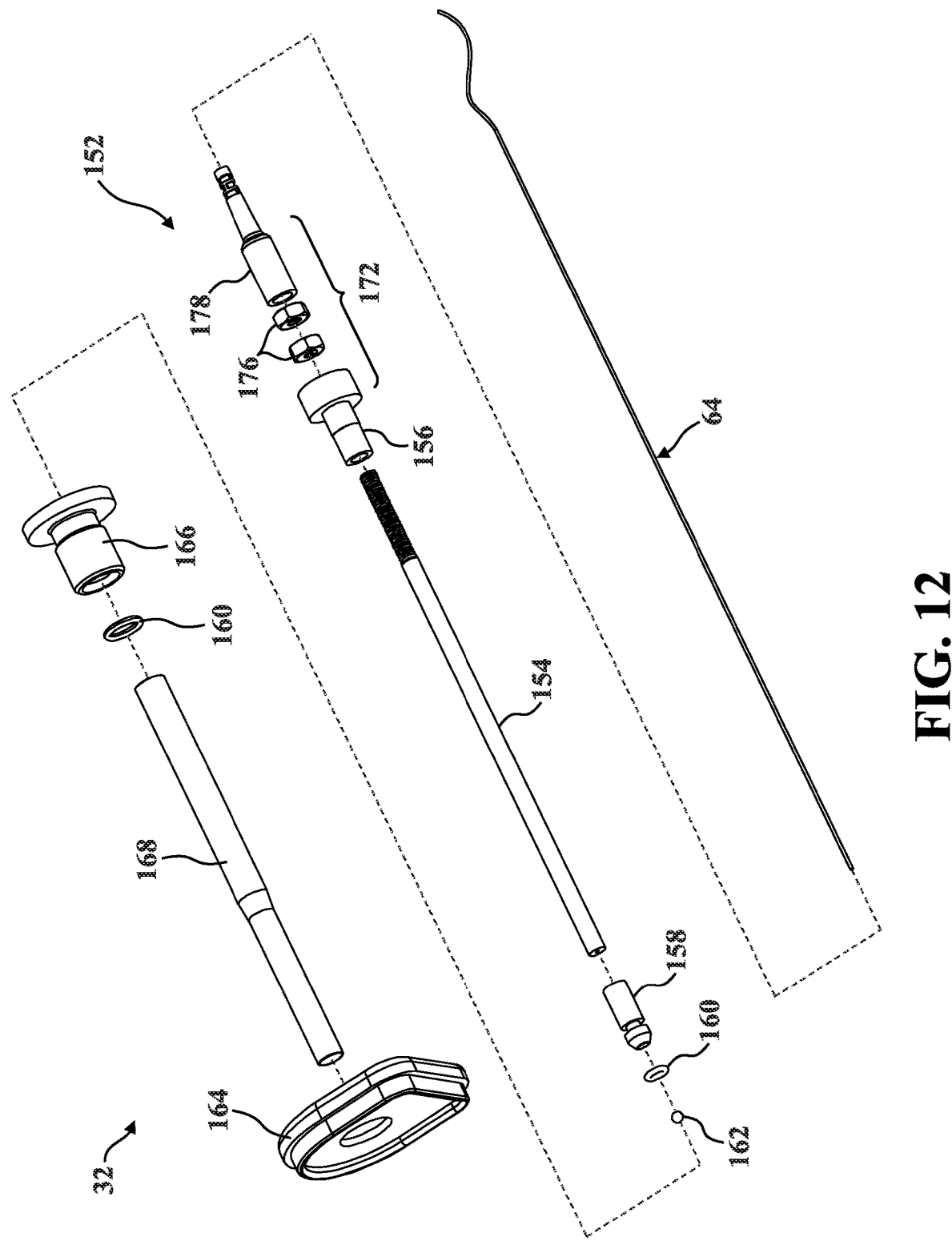
FIG. 12 is a partial exploded perspective view depicting portions of the handpiece of FIG. 10 and showing detail of an adjustment mechanism configured to optically couple to an emission source.
Figure 18:
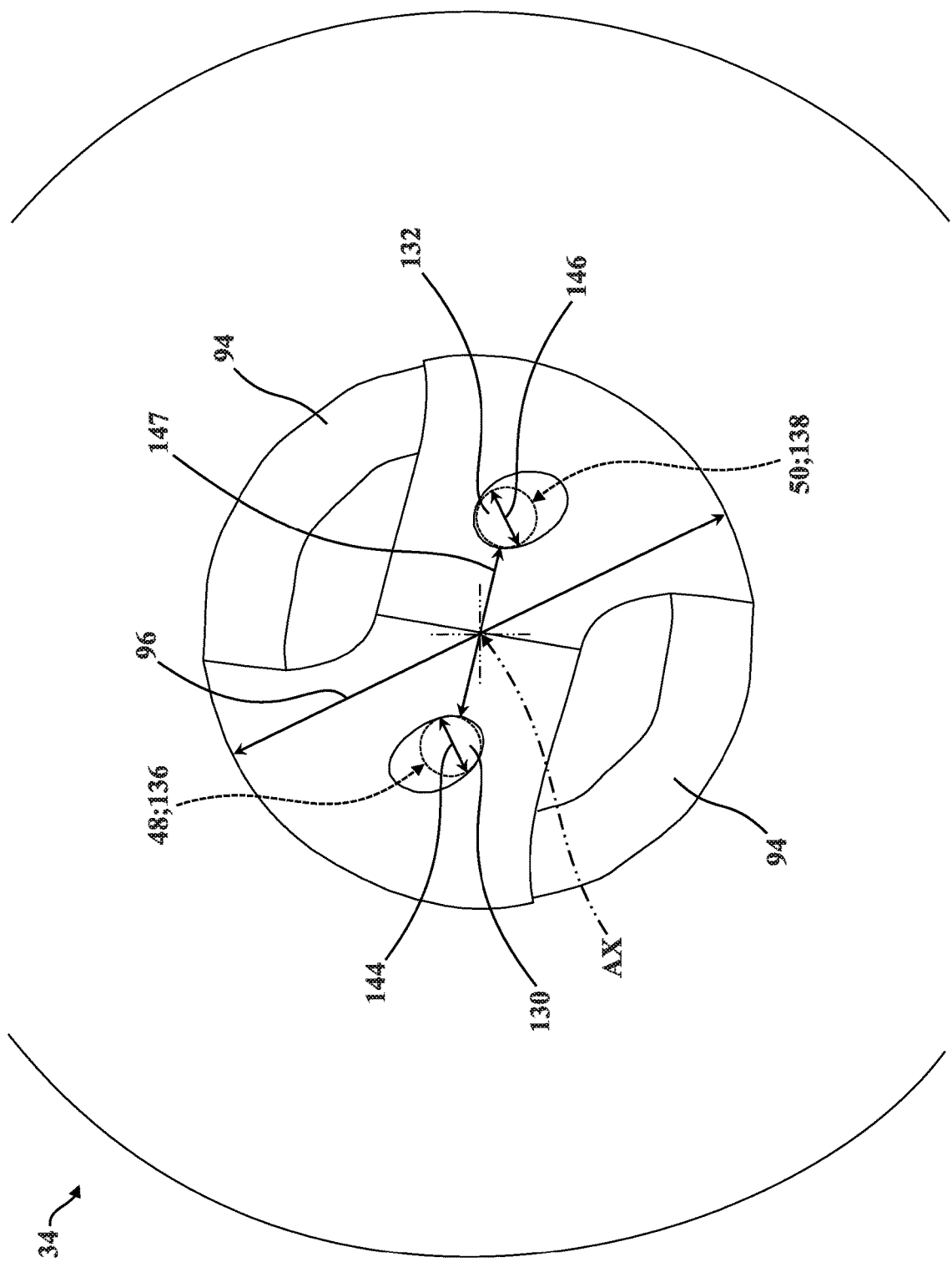
FIG. 18 is a partial front-side view of the tool body of FIGS. 13-17.

In order to facilitate releasable attachment to the chuck assembly 58, the representative embodiment of the tool body 34 depicted in FIGS. 7, 10, and 13-20B is provided with a flat 102 and a relief 104 which help keep the tool body 34 axially and rotatably secured relative to the chuck assembly 58. Those having ordinary skill in the art will recognize this as a conventional surgical chuck configuration, and will appreciate that the chuck assembly 58 could be configured in a number of different ways. Referring now to FIGS. 6-11, the rotary instrument 32 comprises bearings, generally indicated at 106, to help facilitate rotation of the tool body 34 about the axis AX during use. As is best depicted in FIG. 11, the chuck assembly 58 comprises a chuck housing 108 which supports the brace 72 of the detector assembly 46 between a pair of bearings 106. As will be appreciated from the subsequent description below, this arrangement helps reduce vibration and lateral movement of the tool body 34 during rotation which, in turn, helps reduce noise as the detector assembly 46 collects detection data DD. The chuck housing 108 is adapted for removable attachment to the chassis 62 of the handpiece body 52 and generally supports a chuck sleeve 110, a collet 112, and a cap 114, which are coupled to each other with various shims 116, biasing elements 118, and retention clips 120 interposed between certain components to ensure proper retention of the tool body 34 and to reduce noise, vibration, tolerance stack up, and the like.

The chuck sleeve 110 is rotatably supported by the bearings 106 for rotation relative to the chuck housing 108. The chuck sleeve 110 rotates concurrently with the tool body 34 when the tool body 34 is coupled to the rotary instrument 32. As is best depicted in the embodiment illustrated in FIG. 7, the chuck sleeve 110 defines a sleeve aperture 122 positioned so as to be disposed adjacent to the reflector surface 70 of the tool body 34 when the tool body 34 is coupled to the rotary instrument 32. Here, because light exiting the detection lightguide 50 is directed transverse to the axis AX by the reflector surface 70, and because the chuck sleeve 110 and the tool body 34 rotate concurrently, the sleeve aperture 122 is arranged so as to permit light transmitted along the detection lightguide 50 to pass through the sleeve aperture 122 and toward the detector assembly 46 as the rotary instrument 32 rotates the tool body 34.

In the embodiment illustrated in FIG. 7, a sleeve window element 124 is disposed in the sleeve aperture 122 to, among other things, create a physical barrier between the inside of the chuck sleeve 110 and the detector assembly 46, the inside of the chuck housing 108, and the like. Here, the sleeve window element 124 may be configured to focus, direct, or otherwise permit transmission of light from the reflector surface 70 toward the detector assembly 46. Because the detector assembly 46 is disposed adjacent to the recess 68 and the reflector surface 70 of the tool body 34 during use, and because each of the photodetector elements 74 of the detector assembly 46 faces toward the axis AX, light passing through the sleeve aperture 122 is directed toward the detector assembly 46 irrespective of the rotational position of the tool body 34 (see FIGS. 20A-20B), and at least one of the plurality of photodetector elements 74 detects light reflected by the tissue T as the rotary instrument 32 rotates the tool body 34.

As noted above, the chuck sleeve 110 and the tool body 34 rotate concurrently in operation. In order to ensure that the sleeve aperture 122 and the reflector surface 70 are properly aligned so as to transmit light toward the detector assembly 46, the chuck assembly 58 also comprises a plunger 126 and an indexer 128 (see FIGS. 6 and 11). The plunger 126 and the indexer 128 are supported by the collet 112 which, in turn, is pinned or otherwise attached to the cap 114 and helps retain the plunger 126. The plunger 126 is shaped to engage the relief 104 of the tool body 34 to axially align the tool body 34 relative to the chuck sleeve 110. The indexer 128 is configured to abut the flat 102 of the tool body 34 so as to inhibit relative rotation between the tool body 34 and the chuck sleeve 110 during use. However, those having ordinary skill in the art will appreciate that the rotary instrument 32 could employ a chuck assembly 58 that is configured to releasably secure the tool body 34 for rotation in a number of different ways and, thus, could comprise different arrangements and/or types of components.

With continued reference to FIGS. 5-22, as noted above, the emission lightguide 48 and the detection lightguide 50 are each supported within the tool body 34 and are spaced from each other. To this end, the tool body 34 defines an emission channel 130 accommodating the emission lightguide 48 therein, and a detection channel 132 accommodating the detection lightguide 50 therein (see FIG. 2A). In the illustrated embodiments, the emission channel 130 and the detection channel 132 are formed in the bit member 84 of the tool body 34, are spaced from each other about the axis AX, and are disposed helically about the axis AX adjacent to the distal end 34A. Thus, the emission lightguide 48 and the detection lightguide 50 are likewise disposed helically about the axis AX adjacent to the distal end 34A. In order to facilitate ease of manufacture of the tool body 34 and routing of the lightguide 48, 50, a common channel 134 is defined in the shank member 82 of the tool body 34 such that the lightguides 48, 50 exit the respective channels 130, 132 and enter the common channel 134 where the tool body 34 transitions from the bit member 84 to the shank member 82 (see FIGS. 7 and 16). However, it will be appreciated that the lightguides 48, 50 could be routed through, guided by, or otherwise supported by the tool body 34 in a number of different ways.

As is depicted in FIGS. 13-14, the emission channel 130 and the detection channel 132 each extend through the cutting region 92 of the tool body 34 toward the cutting tip face 98. Thus, at least a portion of each of the lightguides 48, 50 similarly extends through the cutting region 92 of the tool body 34, disposed helically about the axis AX adjacent to the distal end 34A. As is depicted in FIG. 19, the emission lightguide 48 extends toward the distal end 34A of the tool body 34 to a distal emission lightguide end 136 adjacent to the cutting tip face 98 so as to position the emission lightguide 48 in contact with tissue T during penetration. Similarly, the detection lightguide 50 extends toward the distal end 34A of the tool body 34 to a distal detection lightguide end 138 adjacent to the cutting tip face 98 so as to position the detection lightguide 50 in contact with tissue T during penetration.

In the embodiment illustrated in FIG. 19, the distal emission lightguide end 136 and the distal detection lightguide end 138 are spaced from the cutting tip face 98. In this embodiment, an emission element 140 is provided extending between the cutting tip face 98 and the distal emission lightguide end 136 to direct light from the emission lightguide 38 to the cutting tip face 98. Similarly, a detection element 142 is provided extending between the cutting tip face and the distal detection lightguide end 138 to direct light reflected toward the cutting tip face 98 toward the detection lightguide 50. This configuration helps prevent wear to the lightguides 48, 50 during use. The emission element 140 and the detection element 142 may be realized as relatively hard, transparent "windows" to prevent wear to the lightguides 48, 50, and promote consistent light transmission out of and into the respective lightguides 48, 50. However, it will be appreciated that the emission element 140 and the detection element 142 can be configured in a number of different ways and, as noted above, could extend to the cutting tip face 98 in some embodiments.

In the representative embodiments illustrated herein, the lightguides 48, 50 are realized as "fiber optic cables" manufactured from plastic, glass, or other materials suitable to promote optical transmission. The emission lightguide 48, the detection lightguide 50, the emission channel 130, and the detection channel 132, each have a generally cylindrical profile. However, other profiles are contemplated. As is depicted with dash-dash lines in FIG. 18, the emission channel 130 defines an emission channel diameter 144 and the detection channel 132 defines a detection channel diameter 146, each of which are less than 25% of the major drill diameter 96 of the tool body 34. In the illustrated embodiment, the emission channel diameter 144 and the detection channel diameter 146 are equal to each other, and the emission channel 130 and the detection channel 132 are spaced from each other at a channel separation distance 147 which is greater than the emission channel diameter 144. However, other configurations are contemplated.

Figure 22:
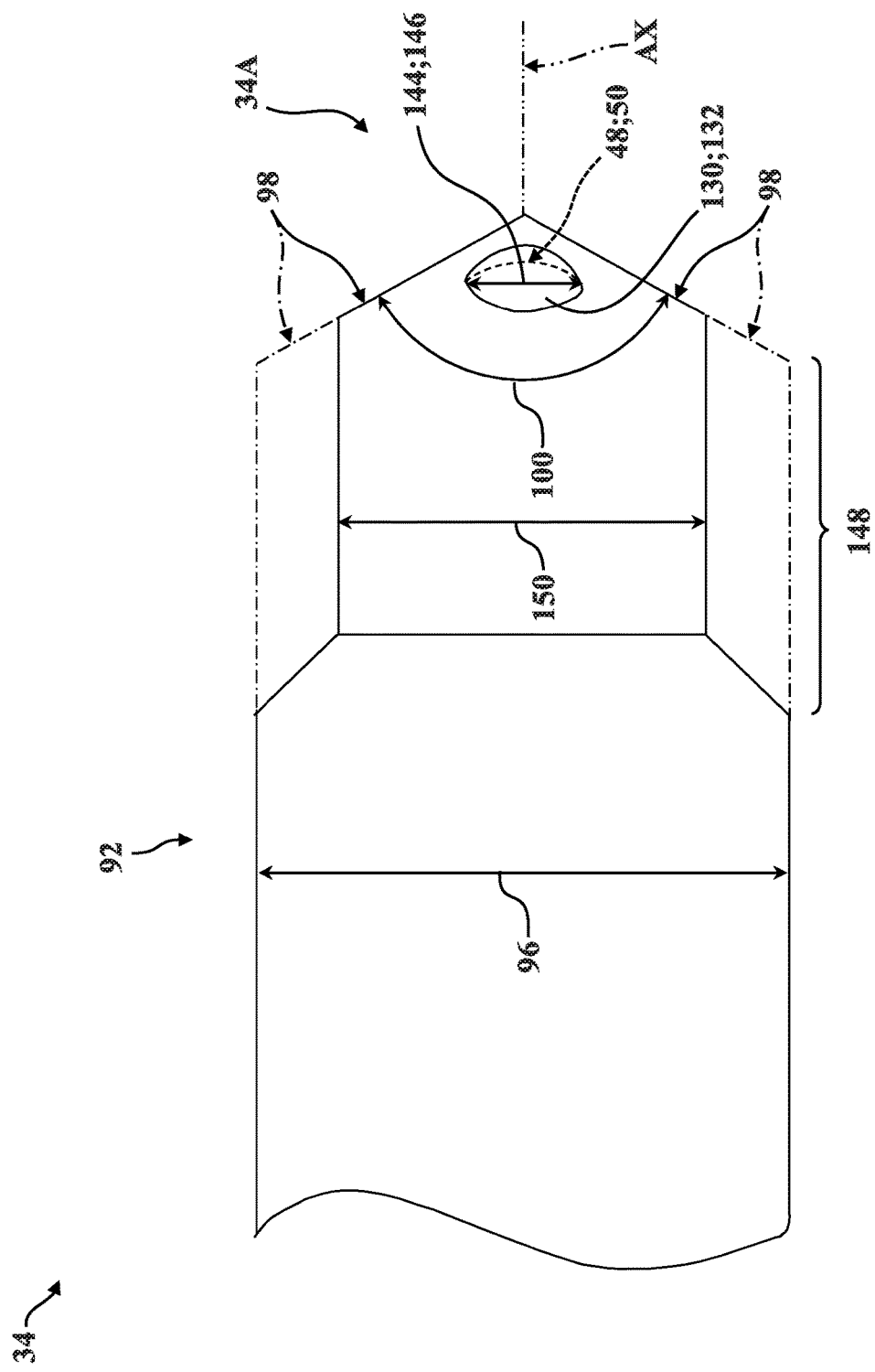
FIG. 22 is a partial schematic view of a stepped distal cutting end of a tool body.

As is depicted with dash-dot-dash lines in the schematic illustration of FIG. 22, the major drill diameter 96 of the tool body 34 can extend along the cutting region 92 up to the cutting tip face 98, or the tool body 34 can comprise a stepped region, generally indicated at 148, adjacent to the distal end 34A. Here, the lightguides 48, 50 each extend through the stepped region toward the cutting tip face 98 at the distal end 34A. The stepped region 148 helps prevent mitigate certain instances of "plunge" during tissue T penetration, as described above, by sizing the cutting tip face 98 to a stepped region diameter 150 which is less than the major drill diameter 96. Thus, in situations where "plunge" cannot be readily avoided, such as where certain layers of tissue T are relatively thin, tissue T damage can be significantly reduced in that the stepped region 148 will penetrate before the major drill diameter 96 of the cutting region 92.

As noted above in connection with the description of FIGS. 1A-1B, the emission source 44 may be integrated within the handpiece body 52 (see FIG. 1A) or may be implemented in the console 40 with the optical tether 64 extending between the console 40 and handpiece body 52 (see FIG. 1B). In the representative embodiment depicted in FIGS. 5-12, the illustrated surgical system 30 is configured for use with an external emission source 44 implemented in the console 40, and employs an optical interface, generally indicated at 152, to facilitate connecting to the optical tether 64. As is best depicted in FIGS. 6, 8-9, and 12, the optical interface 152 may comprise a cannula 154, a mount 156, a tip member 158, one or more seals 160, and an emission lens 162. Here, the optical tether 64 is realized as a fiber optic cable which extends between the emission source 44 in the console 40 (see FIG. 1B) to the emission lens 162. The emission lens 162 directs emitted light toward the emission lightguide 48, as described in greater detail below, and is supported by the tip member 158 which, in turn, is operatively attached to one end of the cannula 154. The cannula 154 has an elongated, generally tubular configuration, is operatively attached to the mount 156, and accommodates the optical tether 64 therein.

The components of the optical interface 152 generally form part of the optical tether 64 and are configured to be removed from the handpiece body 52 in the illustrated embodiment. To this end, the rotary instrument 32 comprises a back plate 164, one or more bushings 166, a receiver 168, and one or more seals 160 to facilitate releasable attachment of the optical interface 152. The back plate 164 is operatively attached to the chassis 62 of the handpiece body 52 and supports one of the bushings 166 which, in turn, supports the receiver 168 (see FIG. 9). The receiver 168 similarly has a tubular profile to receive the optical interface 152, and extends along the axis AX from the back plate 164, through the motor 36, and toward the proximal end 34B of the tool body 34 when the tool body 34 is secured to the rotary instrument 32. Another bushing 166 supports the other end of the receiver 168 and helps keep the receiver 168 aligned relative to the axis AX. As described in greater detail below, the emission lens 162 is configured to direct light emitted from the emission source 44 toward the tool body.

Because the rotary instrument 32 can be configured in a number of different ways, as noted above, it will similarly be appreciated that the optical interface 152 can be configured in a number of different ways sufficient to direct light from the emission source 44 to the proximal end 34B of the tool body 34.

Figure 8:
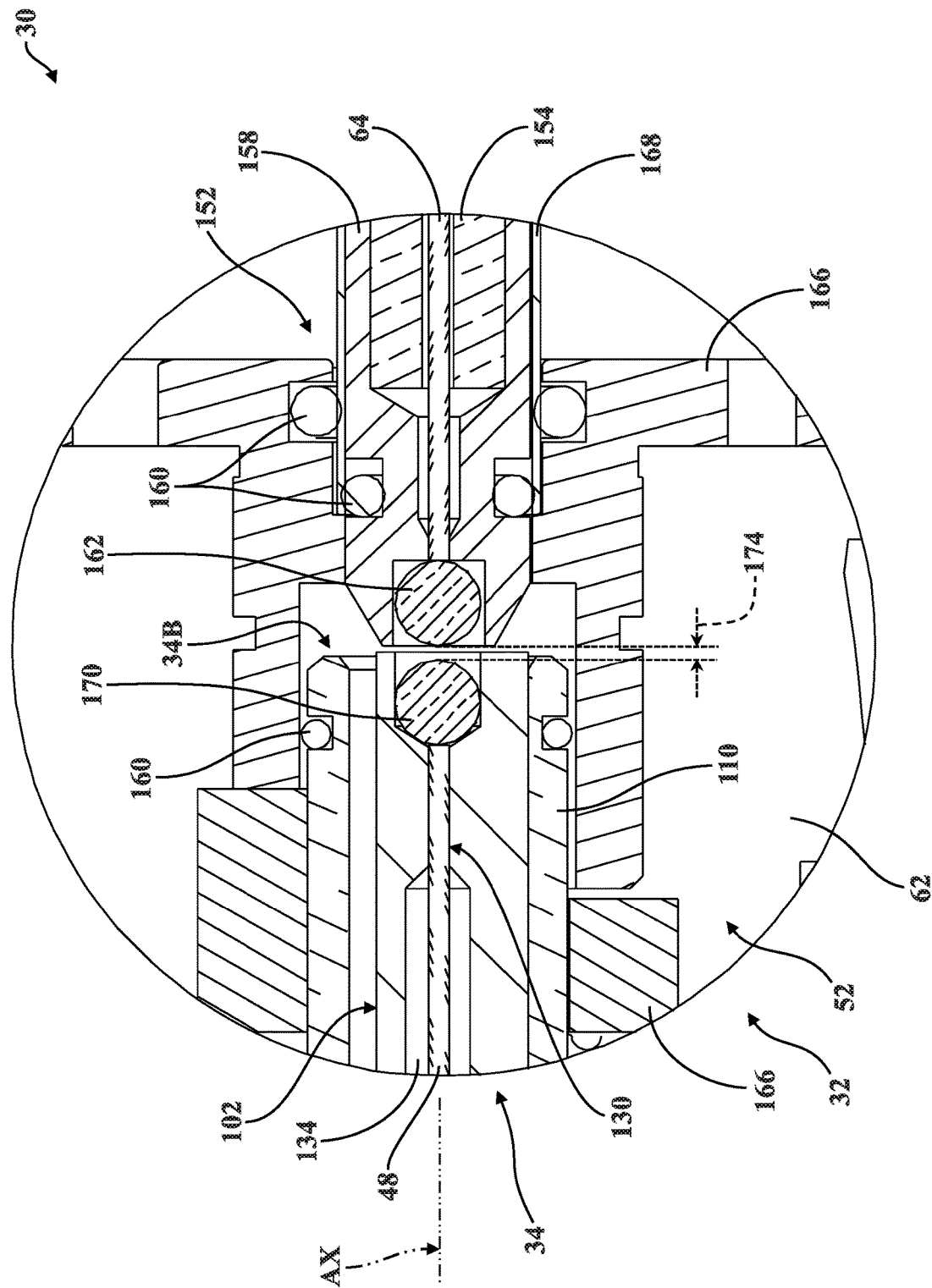
FIG. 8 is a partial section view taken at indicia 8 of FIG. 6.
Figure 9:
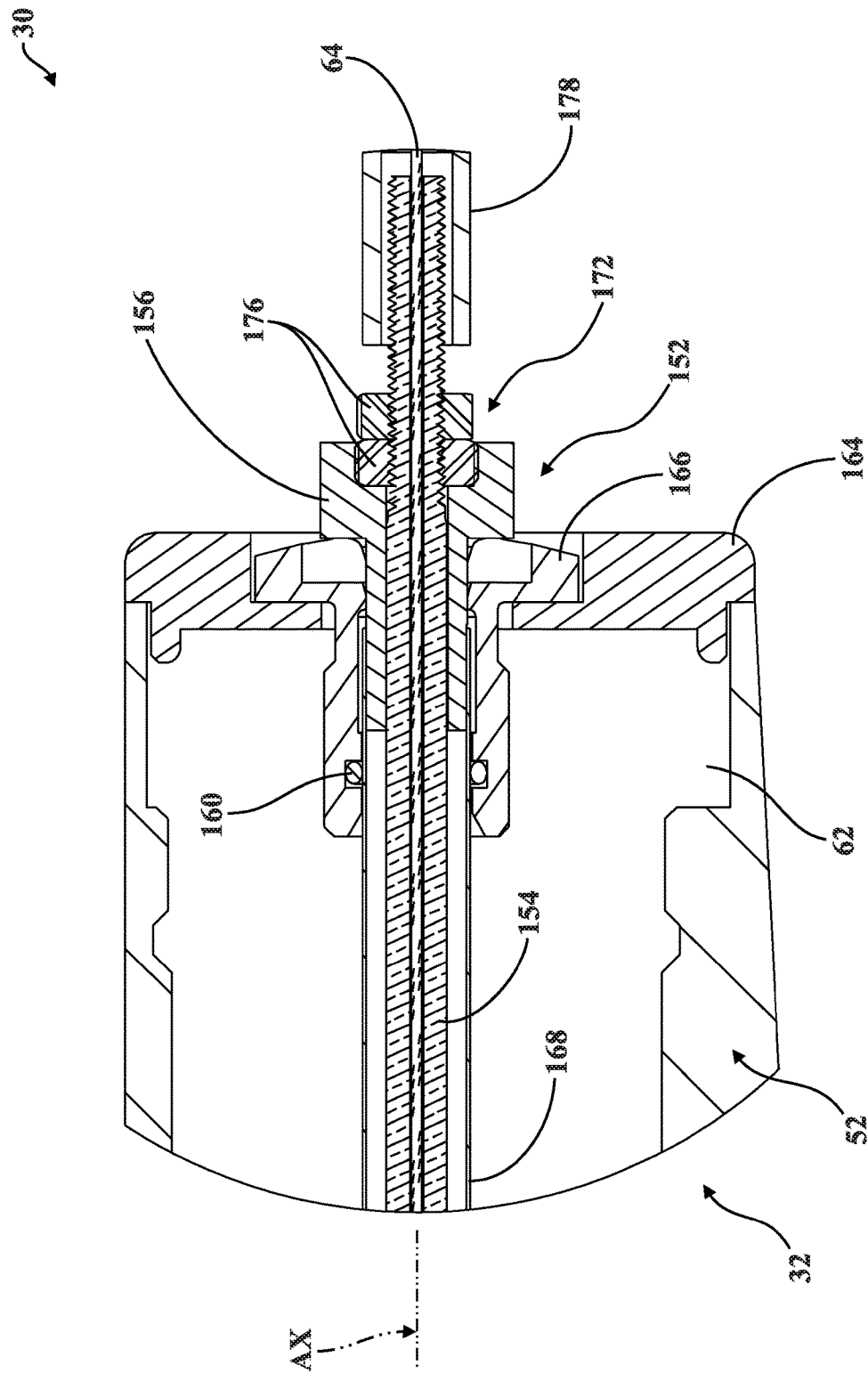
FIG. 9 is a partial section view taken at indicia 9 of FIG. 6.
Figure 10:
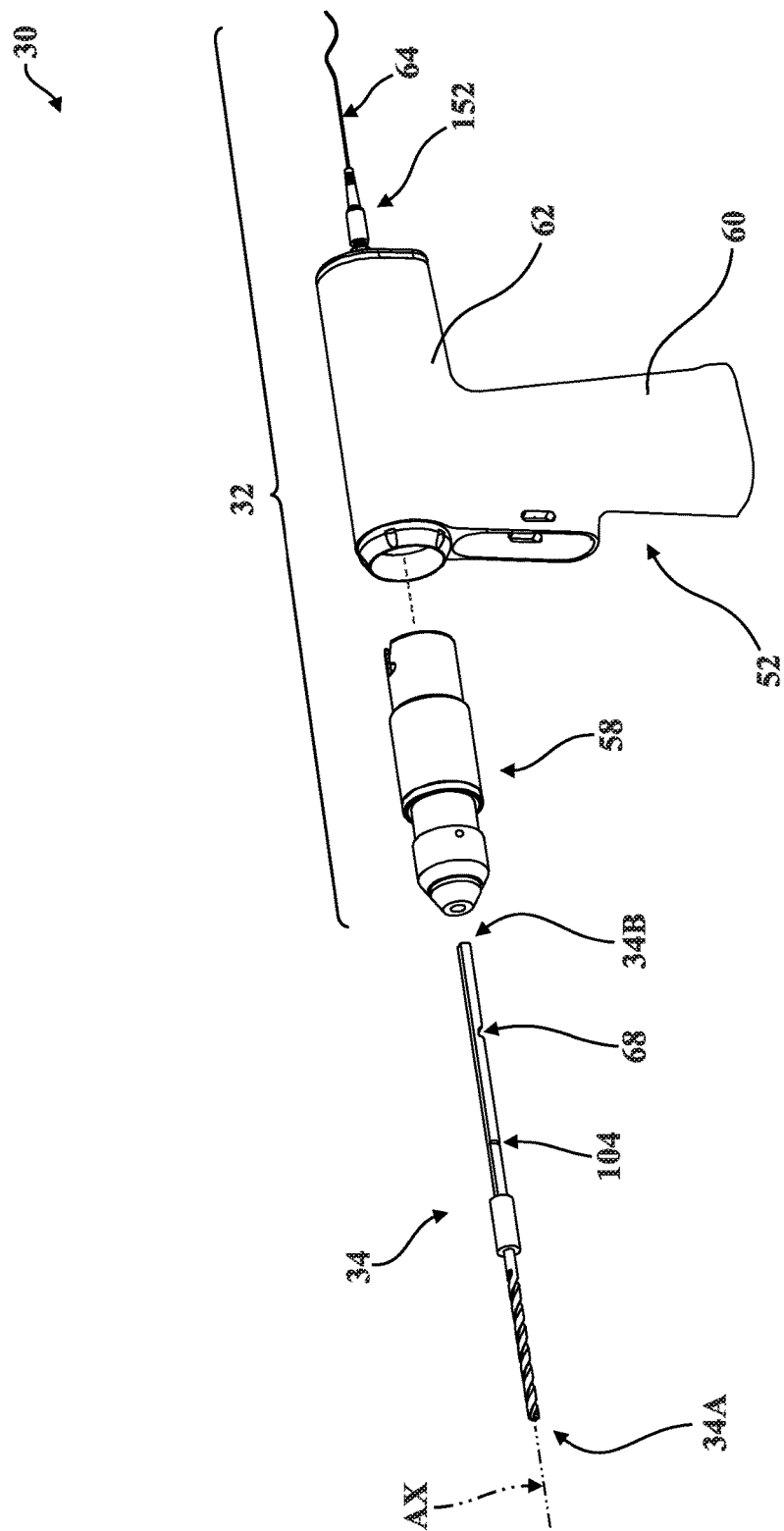
FIG. 10 is a partially-exploded perspective view of the surgical system of FIGS. 5-9, the rotary instrument shown having a chuck assembly spaced from a handpiece and from the tool body.

Referring now to FIG. 8, as noted above, emission lightguide 48 is arranged to receive light from the emission source 44 and directs light along the length of the tool body 34 from the proximal end 34B toward the distal end 34A. To this end, a bit lens 170 may be secured to the proximal end 34B of the tool body 34 to couple light emitted from the emission source 44 into the emission lightguide 48. More specifically, the bit lens 170 and the emission lens 162 cooperate to facilitate transmission of light between the optical interface 152 and the emission lightguide 48. Here, it will be appreciated that optical communication between the bit lens 170 and the emission lens 162 can occur "continuously" during rotation of the tool body 34 because the bit lens 170 and the emission lens 162 are each aligned to the axis AX. In the representative embodiment illustrated throughout the drawings, the emission lens 162 and the bit lens 170 each have a generally spherical profile. However, other configurations are contemplated. In one embodiment, an adjustment mechanism, generally indicated at 172, is interposed between the rotary instrument 32 and the emission lens 162 to maintain a selectable distance 174 between the bit lens 170 and the emission lens 162 (see FIG. 8). To this end, the adjustment mechanism 172 comprises a pair of fasteners 176 disposed in threaded engagement with the cannula 154 adjacent to a flex guide collar 178. The fasteners 176 are movable along the cannula 154 in a "jam nut" arrangement to axially position the cannula 154 relative to the mount 156 which, in turn, adjusts the selectable distance 174. This configuration allows the coupling of light between the bit lens 170 and the emission lens 162 to be fine-tuned or otherwise adjusted to suit different applications. However, it will be appreciated that the adjustment mechanism 172 could be configured in a number of different ways, or omitted for certain applications.

A method of using the surgical system 30 described above is disclosed herein according to one embodiment. The method comprises: driving a rotary instrument 32 to penetrate tissue T; emitting light toward the tissue T at a first wavelength W1; measuring light reflected by the tissue T at a first diffuse reflectance value D1 while emitting light at the first wavelength W1; emitting light toward the tissue T at the second wavelength W2; measuring light reflected by the tissue T at a second diffuse reflectance value D2 while emitting light at the second wavelength W2; generating a waveform WF based on the first diffuse reflectance value D1 and the second diffuse reflectance value D2; analyzing the waveform WF with respect to a tissue boundary threshold TH during tissue T penetration; and controlling the rotary instrument 32 in response to changes in the waveform WF relative to the tissue boundary threshold TH.

Another method of using the surgical system 30 described above is disclosed herein. Here, the method comprises: driving the rotary instrument 32 to penetrate into tissue T; emitting light toward the tissue T with an emission source 44; measuring light reflected by the tissue T with a detector assembly 46 at a diffuse reflectance value D1; generating a waveform WF via the controller based on the diffuse reflectance value D1; determining a patient-specific bone characteristic BC based on the diffuse reflectance value; adjusting the waveform WF based on the patient-specific bone characteristic BC; analyzing the adjusted waveform WF with respect to a tissue boundary threshold TH during penetration; and controlling the rotary instrument 32 in response to changes in the adjusted waveform WF relative to the tissue boundary threshold TH. In one embodiment, penetrating the tissue T comprises penetrating a first bone layer (or, a "first material layer"), penetrating marrow TM (or, a "second material layer"), and penetrating a second bone layer (or, a "third material layer"). In one embodiment, determining the patient-specific bone characteristic BC (or, the "workpiece-specific material characteristic") occurs prior to penetration of the second bone layer, and adjustment of the waveform WF is based on the patient-specific bone characteristic BC of the first bone layer. Here, as noted above, the patient-specific bone characteristic BC can be employed to help facilitate precise tissue T penetration based on the patient's anatomy.

In this way, the surgical system 30 described above improves the safety and reliability of tissue T penetration by allowing different kinds of tissue boundaries TB to be detected during tissue T penetration reliably and quickly, thereby significantly reducing the risk of unintended "plunge" across tissue boundaries TB. Specifically, those having ordinary skill in the art will appreciate that the configuration of the surgical system 30 allows for "continuous" emission of light out of the emission lightguide 48 and detection of light reflected by the tissue T by the detector assembly 46 during rotation of the tool body 34. Moreover, it will be appreciated that the normalization of the first and second diffuse reflectance values D1, D2 afforded by the waveform WF contributes to reduced noise and improved tissue boundary TB detection accuracy. It will be appreciated that the surgical system 30 affords significant opportunities for promoting improved intraoperative patient safety and successful postoperative patient recovery, and may be particularly advantageous with relatively "high risk" surgical interventions, such as those involving cranial perforation, vertebral pedicle screw placement, and the like. Nevertheless, the surgical system 30 of the present disclosure can be utilized in a simple, reliable, and efficient manner for a broad number of different medical and/or surgical procedures which involve tissue T penetration.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

I. A surgical system for penetrating tissue of a patient and for determining a characteristic of the tissue, said surgical system comprising:

a rotary instrument to generate rotational torque;

an emission source operatively coupled to said rotary instrument to emit light;

a detector assembly operatively coupled to said rotary instrument to detect light;

a drill bit comprising a tool body extending along an axis between a distal end to engage the tissue and a proximal end to releasably couple to said rotary instrument;

an emission lightguide supported within said tool body and disposed in optical communication with said emission source when said tool body is coupled to said rotary instrument to transmit light emitted by said emission source though said emission lightguide and toward the tissue as said rotary instrument rotates said tool body; and a detection lightguide supported within said tool body, spaced from said emission lightguide, and disposed in optical communication with said detector assembly when said tool body is coupled to said rotary instrument to transmit light reflected by the tissue through said detection lightguide and toward said detector assembly as said rotary instrument rotates said tool body;

wherein said emission source emits light into said emission lightguide along said axis, and said detector assembly is arranged to detect light reflected from the tissue exiting said detection lightguide transverse to said axis when said tool body is coupled to said rotary instrument.

II. The surgical system as set forth in clause I, wherein said tool body of said drill bit defines a recess formed transverse to said axis and arranged between said distal end and said proximal end with said detection lightguide extending along said tool body from said distal end to said recess.

III. The surgical system as set forth in clause II, wherein said tool body of said drill bit comprises a reflector surface positioned within said recess to direct light transmitted along said detection lightguide toward said detector assembly.

IV. The surgical system as set forth in clause III, wherein said rotary instrument comprises a bearing to operatively support said tool body for rotation about said axis; and wherein said detector assembly is disposed adjacent to said bearing and is arranged adjacent to said recess to detect light reflected by the tissue and transmitted along said detection lightguide.

V. The surgical system as set forth in any one of clauses I-IV, wherein said emission source comprises:

a first light source to emit light into said emission lightguide at a first wavelength; and a second light source to emit light into said emission lightguide at a second wavelength different from said first wavelength.

VI. The surgical system as set forth in clause V, wherein said first wavelength is absorbable by blood and said second wavelength is less absorbable by blood than said first wavelength.

VII. The surgical system as set forth in any one of clauses I-VI, wherein said tool body of said drill bit defines an emission channel accommodating said emission lightguide therein, and a detection channel accommodating said detection lightguide therein.

VIII. The surgical system as set forth in clause VII, wherein said tool body of said drill bit defines a cutting region adjacent to said distal end shaped to promote tissue penetration.

IX. The surgical system as set forth in clause VIII, wherein said tool body of said drill bit comprises flutes formed along said cutting region to direct tissue away from said distal end and toward said proximal end.

X. The surgical system as set forth in any one of clauses VIII-IX, wherein said cutting region of said tool body defines a major drill diameter; and wherein said cutting region of said tool body comprises a cutting tip face formed at a tip angle defined between said distal end and said major drill diameter.

XI. The surgical system as set forth in clause X, wherein said emission channel and said detection channel each extend through said cutting region of said tool body toward said cutting tip face.

XII. The surgical system as set forth in clause XI, wherein said emission lightguide extends toward said distal end to a distal emission lightguide end adjacent to said cutting tip face to position said emission lightguide in contact with the tissue during tissue penetration; and wherein said detection lightguide extends toward said distal end to a distal detection lightguide end adjacent to said cutting tip face to position said detection lightguide in contact with the tissue during tissue penetration.

XIII The surgical system as set forth in clause XI, wherein said emission lightguide extends toward said distal end to a distal emission lightguide end spaced from said cutting tip face to position said emission lightguide out of contact with the tissue during tissue penetration;

wherein said detection lightguide extends toward said distal end to a distal detection lightguide end spaced from said cutting tip face to position said detection lightguide out of contact with the tissue during tissue penetration; and further comprising an emission element extending between said cutting tip face and said distal emission lightguide end to direct light from said emission lightguide to said cutting tip face, and a detection element extending between said cutting tip face and said distal detection lightguide end to direct light reflected toward said cutting tip face to said detection lightguide.

XIV. A drill bit for penetrating tissue of a patient and for use with a surgical system adapted to determine a characteristic of the tissue, the surgical system including a rotary instrument with an emission source to emit light and a detector assembly to detect light, said drill bit comprising:

a tool body extending along an axis between a distal end to engage the tissue and a proximal end to releasably couple to the rotary instrument, said tool body defining a recess formed transverse to said axis and arranged between said distal end and said proximal end;

an emission lightguide supported within said tool body, extending along said tool body from said proximal end to said distal end, and disposed in optical communication with the emission source when said tool body is coupled to the rotary instrument to transmit light emitted by the emission source through said emission lightguide and toward the tissue as the rotary instrument rotates said tool body; and a detection lightguide supported within said tool body, spaced from said emission lightguide, extending along said tool body from said distal end to said recess, and disposed in optical communication with the detector assembly when said tool body is coupled to the rotary instrument to transmit light reflected by the tissue through said detection lightguide and toward the detector assembly as the rotary instrument rotates said tool body;

wherein said emission lightguide and said detection lightguide are each disposed helically about said axis adjacent to said distal end of said tool body.

XV. The drill bit as set forth in clause XIV, wherein said tool body defines an emission channel accommodating said emission lightguide therein, and a detection channel accommodating said detection lightguide therein.

XVI. The drill bit as set forth in any one of clauses XIV-XV, wherein said tool body defines a cutting region adjacent to said distal end shaped to promote tissue penetration.

XVII. The drill bit as set forth in clause XVI, wherein said tool body comprises flutes formed along said cutting region to direct tissue away from said distal end and toward said proximal end.

XVIII. The drill bit as set forth in any one of clauses XV-XVII, wherein said cutting region of said tool body defines a major drill diameter; and wherein said cutting region of said tool body comprises a cutting tip face formed at a tip angle defined between said distal end and said major drill diameter.

XIX. The drill bit as set forth in clause XVIII, wherein said emission channel and said detection channel each extend through said cutting region of said tool body toward said cutting tip face.

XX. The drill bit as set forth in clause XIX, wherein said emission lightguide extends toward said distal end to a distal emission lightguide end adjacent to said cutting tip face to position said emission lightguide in contact with the tissue during tissue penetration; and wherein said detection lightguide extends toward said distal end to a distal detection lightguide end adjacent to said cutting tip face to position said detection lightguide in contact with the tissue during tissue penetration.

XXI. The drill bit as set forth in clause XIX, wherein said emission lightguide extends toward said distal end to a distal emission lightguide end spaced from said cutting tip face to position said emission lightguide out of contact with the tissue during tissue penetration;

wherein said detection lightguide extends toward said distal end to a distal detection lightguide end spaced from said cutting tip face to position said detection lightguide out of contact with the tissue during tissue penetration; and further comprising an emission element extending between said cutting tip face and said distal emission lightguide end to direct light from said emission lightguide to said cutting tip face, and a detection element extending between said cutting tip face and said distal detection lightguide end to direct light reflected toward said cutting tip face to said detection lightguide.

XXII. A surgical system for penetrating tissue of a patient and for detecting boundaries between different tissues, said surgical system comprising:

a rotary instrument to generate rotational torque;

a drill bit extending along an axis between a distal end to engage tissue and a proximal end to releasably couple to said rotary instrument;

a first light source operatively coupled to said rotary instrument to emit light at a first wavelength;

a second light source operatively coupled to said rotary instrument to emit light at a second wavelength different from said first wavelength;

a detector assembly operatively coupled to said rotary instrument to detect light reflected by the tissue; and a controller in communication with said rotary instrument, said first light source, said second light source, and said detector assembly;

wherein said controller is configured to measure a first diffuse reflectance value with said detector assembly while driving said first light source, to measure a second diffuse reflectance value with said detector assembly while driving said second light source, to generate a waveform based on said first diffuse reflectance value and said second diffuse reflectance value, and to analyze said waveform to detect a tissue boundary threshold during tissue penetration with said drill bit and to control said rotary instrument in response to said detection.

XXIII. The surgical system as set forth in clause XXII, wherein said controller is further configured to interrupt said rotary instrument in response to said waveform exceeding said tissue boundary threshold.

XXIV. The surgical system as set forth in any one of clauses XXII-XXIII, wherein said controller is configured to asynchronously drive said first light source and said second light source to sequentially emit light toward the tissue at said first wavelength and at said second wavelength.

XXV. The surgical system as set forth in any one of clauses XXII-XXIV, wherein said controller is configured to generate said waveform based at least partially on a ratio of said first diffuse reflectance value to said second diffuse reflectance value.

XXVI. The surgical system as set forth in clause XXV, wherein said controller is configured to analyze said waveform during tissue penetration for changes in said ratio occurring over time.

XXVII. The surgical system as set forth in any one of clauses XXII-XXVI, wherein said first wavelength is absorbable by blood and said second wavelength is less absorbable by blood than said first wavelength.

XXVIII. The surgical system as set forth in any one of clauses XXII-XXVII, wherein said tissue boundary threshold represents a boundary between two types of tissue selected from a group consisting of bone, marrow, muscle, nerve, epithelial, and connective.

XXIX. The surgical system as set forth in any one of clauses XXII-XXVII, wherein said tissue boundary threshold represents a boundary between periosteum and cortical bone.

XXX. The surgical system as set forth in any one of clauses XXII-XXVII, wherein said tissue boundary threshold represents a boundary between cortical bone and trabecular bone.

XXXI. The surgical system as set forth in any one of clauses XXII-XXVII, wherein said tissue boundary threshold represents a boundary between trabecular bone and marrow.

XXXII. A surgical system for penetrating tissue of a patient and for determining a characteristic of the tissue, said surgical system comprising:

a rotary instrument to generate rotational torque;

a drill bit comprising a tool body extending along an axis between a distal end to engage the tissue and a proximal end to releasably couple to said rotary instrument;

an emission source operatively coupled to said rotary instrument to emit light parallel to said axis;

a detector assembly operatively coupled to said rotary instrument to detect light transverse to said axis;

an emission lightguide supported within said tool body and disposed in optical communication with said emission source when said tool body is coupled to said rotary instrument to transmit light emitted by said emission source though said emission lightguide and toward the tissue as said rotary instrument rotates said tool body; and a detection lightguide supported within said tool body, spaced from said emission lightguide, and disposed in optical communication with said detector assembly when said tool body is coupled to said rotary instrument to transmit light reflected by the tissue through said detection lightguide and toward said detector assembly as said rotary instrument rotates said tool body;

wherein said detector assembly comprises a brace supporting a plurality of photodetector elements facing said axis to detect light transmitted through said detection lightguide and exiting said detection lightguide transverse to said axis such that at least one of said plurality of photodetector elements detects light reflected by the tissue as said rotary instrument rotates said tool body.

XXXIII. A method of using a surgical system to penetrate tissue of a patient and to detect boundaries between different tissues, said method comprising:

driving a rotary instrument to penetrate bone tissue;
emitting light toward the bone tissue at a first wavelength;
measuring light reflected by the bone tissue at a first diffuse reflectance value while emitting light at the first wavelength;
emitting light toward the bone tissue at a second wavelength;
measuring light reflected by the bone tissue at a second diffuse reflectance value while emitting light at the second wavelength;
generating a waveform based on the first diffuse reflectance value and the second diffuse reflectance value;
analyzing the waveform with respect to a tissue boundary threshold during bone tissue penetration;
controlling the rotary instrument in response to changes in the waveform relative to the tissue boundary threshold.

XXXIV. A method of using a surgical system to penetrate tissue of a patient and to determine a characteristic of the tissue, said method comprising:

driving the rotary instrument to penetrate into tissue;
emitting light toward the tissue with an emission source;
measuring light reflected by the tissue with a detector assembly at a diffuse reflectance value;
generating a waveform via a controller based on the diffuse reflectance value;
determining a patient-specific bone characteristic based on the diffuse reflectance value;
adjusting the waveform based on the patient-specific bone characteristic;
analyzing the adjusted waveform with respect to a tissue boundary threshold during penetration;
controlling the rotary instrument in response to changes in the adjusted waveform relative to the tissue boundary threshold.

XXXV. The method as set forth in clause XXXIV, wherein penetrating tissue comprises penetrating a first bone layer, penetrating marrow, and penetrating a second bone layer.

XXXVI. The method as set forth in clause XXXV, wherein determining the patient-specific bone characteristic occurs prior to penetration of the second bone layer; and wherein adjustment of the waveform is based on the patient-specific bone characteristic of the first bone layer.

The invention claimed is:

1. A surgical system for penetrating material of a workpiece and for determining a characteristic of the material, said surgical system comprising:

a rotary instrument to generate rotational torque;
an emission source operatively coupled to said rotary instrument to emit light;
a detector assembly operatively coupled to said rotary instrument to detect light;
a drill bit comprising a tool body extending along an axis between a distal end to engage the material and a proximal end to releasably couple to said rotary instrument;
an emission lightguide supported within said tool body and disposed in optical communication with said emission source when said tool body is coupled to said rotary instrument to transmit light emitted by said emission source through said emission lightguide and toward the material as said rotary instrument rotates said tool body; and
a detection lightguide supported within said tool body, spaced from said emission lightguide, and disposed in optical communication with said detector assembly when said tool body is coupled to said rotary instrument to transmit light reflected by the material through said detection lightguide and toward said detector assembly as said rotary instrument rotates said tool body;
wherein said emission source emits light into said emission lightguide along said axis, and said detector assembly is arranged to detect light reflected from the material exiting said detection lightguide transverse to said axis when said tool body is coupled to said rotary instrument.

2. The surgical system as set forth in claim 1, wherein said tool body of said drill bit defines a recess formed transverse to said axis and arranged between said distal end and said proximal end with said detection lightguide extending along said tool body from said distal end to said recess.

3. The surgical system as set forth in claim 2, wherein said tool body of said drill bit comprises a reflector surface positioned within said recess to direct light transmitted along said detection lightguide toward said detector assembly.

4. The surgical system as set forth in claim 3, wherein said detector assembly comprises a brace supporting a plurality of photodetector elements arranged facing said axis to detect light directed from said reflector surface as said rotary instrument rotates said tool body.

5. The surgical system as set forth in claim 3, wherein said rotary instrument comprises a bearing to operatively support said tool body for rotation about said axis; and wherein said detector assembly is disposed adjacent to said bearing and is arranged adjacent to said recess to detect light reflected by the material and transmitted along said detection lightguide.

6. The surgical system as set forth in claim 5, wherein said rotary instrument further comprises a chuck assembly to releasably secure said tool body for rotation; and wherein said chuck assembly comprises a chuck housing supporting said bearing and said detector assembly.

7. The surgical system as set forth in claim 6, wherein said chuck assembly further comprises a chuck sleeve rotatably supported by said bearing to rotate concurrently with said tool body when said tool body is coupled to said rotary instrument.

8. The surgical system as set forth in claim 7, wherein said chuck sleeve defines a sleeve aperture positioned adjacent to said reflector surface when said tool body is coupled to said rotary instrument to permit light transmitted along said detection lightguide to pass through said sleeve aperture and toward said detector assembly as said rotary instrument rotates said tool body.

9. The surgical system as set forth in claim 1, wherein said emission source comprises:

a first light source to emit light into said emission lightguide at a first wavelength; and a second light source to emit light into said emission lightguide at a second wavelength different from said first wavelength.

10. The surgical system as set forth in claim 9, wherein said first wavelength and said second wavelength are each between 400 nm and 1000 nm.

11. The surgical system as set forth in claim 9, further comprising a controller in communication with said first light source and said second light source, said controller being configured to asynchronously drive said first light source and said second light source to sequentially emit light into said emission lightguide at said first wavelength and at said second wavelength.

12. The surgical system as set forth in claim 11, wherein said controller is configured to generate a first square wave to drive said first light source, and to generate a second square wave to drive said second light source.

13. The surgical system as set forth in claim 12, wherein said first square wave and said second square wave are 180-degrees out of phase with each other.

14. The surgical system as set forth in claim 11, wherein said controller is configured to drive said first light source and said second light source at an emission frequency; and
wherein said controller is configured to acquire detection data from said detector assembly at a detection frequency, said detection frequency being twice said emission frequency.

15. The surgical system as set forth in claim 14, wherein said emission frequency is greater than 100 Hz.

16. The surgical system as set forth in claim 11, wherein said controller is configured to acquire detection data from said detector assembly each time one of said first light source and said second light source emits light.

17. The surgical system as set forth in claim 1, wherein said tool body of said drill bit defines an emission channel accommodating said emission lightguide therein, and a detection channel accommodating said detection lightguide therein, and wherein said tool body of said drill bit defines a cutting region adjacent to said distal end shaped to promote material penetration, and wherein said cutting region of said tool body defines a major drill diameter, and wherein said cutting region of said tool body comprises a cutting tip face formed at a tip angle defined between said distal end and said major drill diameter, and wherein said emission channel and said detection channel each extend through said cutting region of said tool body toward said cutting tip face, and wherein said emission lightguide extends toward said distal end to a distal emission lightguide end spaced from said cutting tip face to position said emission lightguide out of contact with the material during material penetration, and wherein said detection lightguide extends toward said distal end to a distal detection lightguide end spaced from said cutting tip face to position said detection lightguide out of contact with the material during material penetration, and further comprising an emission element extending between said cutting tip face and said distal emission lightguide end to direct light from said emission lightguide to said cutting tip face, and a detection element extending between said cutting tip face and said distal detection lightguide end to direct light reflected toward said cutting tip face to said detection lightguide.

18. The surgical system as set forth in claim 1, wherein said tool body of said drill bit comprises a stepped region adjacent to said distal end with said emission lightguide and said detection lightguide each extending through said stepped region toward said distal end.

19. The surgical system as set forth in claim 1, further comprising a bit lens secured to said proximal end of said tool body to couple light emitted from said emission source into said emission lightguide, and further comprising an emission lens secured to said rotary instrument and disposed in optical communication with said emission source to direct light emitted from said emission source toward said bit lens, and further comprising an adjustment mechanism interposed between said rotary instrument and said emission lens to maintain a selectable distance between said bit lens and said emission lens.

20. A surgical system for penetrating material of a workpiece and for detecting boundaries between different materials, said surgical system comprising:
a rotary instrument to generate rotational torque;
a drill bit extending along an axis between a distal end to engage material and a proximal end to releasably couple to said rotary instrument;
a first light source operatively coupled to said rotary instrument to emit light at a first wavelength;
a second light source operatively coupled to said rotary instrument to emit light at a second wavelength different from said first wavelength;
a detector assembly operatively coupled to said rotary instrument to detect light reflected by the material; and
a controller in communication with said rotary instrument, said first light source, said second light source, and said detector assembly;
wherein said controller is configured to measure a first diffuse reflectance value with said detector assembly while driving said first light source, to measure a second diffuse reflectance value with said detector assembly while driving said second light source, to generate a waveform based on said first diffuse reflectance value and said second diffuse reflectance value, and to analyze said waveform to detect a material boundary threshold during material penetration with said drill bit and to control said rotary instrument in response to said detection.

21. A method of using a surgical system to penetrate material of a workpiece and to determine a characteristic of the material, said method comprising:
driving a rotary instrument of the surgical system to penetrate into material;
emitting light toward the material with an emission source;
measuring light reflected by the material with a detector assembly at a diffuse reflectance value;
generating a waveform via a controller based on the diffuse reflectance value;
determining a workpiece-specific material characteristic based on the diffuse reflectance value;
adjusting the waveform based on the workpiece-specific material characteristic;
analyzing the adjusted waveform with respect to a material boundary threshold during penetration;
controlling the rotary instrument in response to changes in the adjusted waveform relative to the material boundary threshold.

* * * * *